(12) United States Patent
Shaw et al.

(10) Patent No.: US 9,956,352 B2
(45) Date of Patent: May 1, 2018

(54) COMBINED MEDICAL DEVICE WITH SLIDING FRONTAL ATTACHMENT AND RETRACTABLE NEEDLE

(71) Applicants: Retractable Technologies, Inc., Little Elm, TX (US); Thomas J. Shaw, Frisco, TX (US)

(72) Inventors: Thomas J Shaw, Frisco, TX (US); Mark Small, Heavener, OK (US); Ni Zhu, Plano, TX (US)

(73) Assignee: Retractable Technologies, Inc., Little Elm, TX (US)

( * ) Notice: Subject to any disclaimer, the term of this patent is extended or adjusted under 35 U.S.C. 154(b) by 135 days.

(21) Appl. No.: 14/020,465

(22) Filed: Sep. 6, 2013

(65) Prior Publication Data

US 2014/0171876 A1 Jun. 19, 2014

Related U.S. Application Data

(63) Continuation-in-part of application No. 13/714,819, filed on Dec. 14, 2012.

(60) Provisional application No. 61/737,263, filed on Dec. 14, 2012, provisional application No. 61/836,723, filed on Jun. 19, 2013.

(51) Int. Cl.
*A61M 5/32* (2006.01)
*A61B 5/15* (2006.01)
*A61B 5/153* (2006.01)
*A61M 25/06* (2006.01)

(52) U.S. Cl.
CPC ....... *A61M 5/3221* (2013.01); *A61B 5/15003* (2013.01); *A61B 5/153* (2013.01); *A61B 5/150236* (2013.01); *A61B 5/150244* (2013.01); *A61B 5/150259* (2013.01); *A61B 5/150389* (2013.01); *A61B 5/150503* (2013.01); *A61B 5/150587* (2013.01); *A61B 5/150656* (2013.01); *A61B 5/150717* (2013.01); *A61M 5/3232* (2013.01); *A61M 5/3202* (2013.01);
(Continued)

(58) Field of Classification Search
CPC ...... A61M 5/32; A61M 5/3206; A61M 5/322; A61M 5/3221
See application file for complete search history.

(56) References Cited

U.S. PATENT DOCUMENTS 2,168,686 A 8/1939 Saffir
4,367,737 A 1/1983 Kozam et al.
(Continued)

FOREIGN PATENT DOCUMENTS

EP 0479303 8/1992
EP 1161962 12/2001

*Primary Examiner* — Daniel Cerioni
*Assistant Examiner* — Yasmeen S Warsi
(74) *Attorney, Agent, or Firm* — Ross Barnes LLP; Monty L. Ross; Robin L. Barnes

(57) ABSTRACT

A medical device having a frontal attachment and a connector housing having at least a body part of an associated medical apparatus, the frontal attachment slidably engaging the connector housing and having a forwardly projecting, rearwardly biased needle and a needle retraction assembly, and the connector housing having a needle retraction cavity laterally offset from the needle in a first position, the needle retraction cavity being selectively movable relative to the frontal attachment following use to reposition the needle retraction cavity into alignment with the needle to permit retraction.

14 Claims, 22 Drawing Sheets

(52) U.S. Cl.
CPC ..... *A61M 25/0606* (2013.01); *A61M 25/0631* (2013.01); *A61M 2005/3227* (2013.01)

(56) References Cited

U.S. PATENT DOCUMENTS

| | | | |
|---|---|---|---|
| 4,610,666 A | 9/1986 | Pizzino | |
| 4,747,831 A | 5/1988 | Kulli | |
| 4,813,426 A | 3/1989 | Haber et al. | |
| 4,941,883 A | 7/1990 | Venturini | |
| 4,973,316 A | 11/1990 | Dysarz | |
| D326,154 S | 5/1992 | Deguchi et al. | |
| 5,151,089 A * | 9/1992 | Kirk, III | A61M 5/3216 604/192 |
| 5,163,916 A | 11/1992 | Sunderland | |
| 5,263,942 A | 11/1993 | Smedley et al. | |
| 5,298,023 A | 3/1994 | Haber et al. | |
| 5,312,351 A | 5/1994 | Gerrone | |
| 5,354,284 A | 10/1994 | Haber et al. | |
| 5,370,628 A | 12/1994 | Allison et al. | |
| 5,395,337 A | 3/1995 | Clemens et al. | |
| 5,423,758 A | 6/1995 | Shaw | |
| 5,445,618 A | 8/1995 | Adobbati | |
| 5,503,010 A | 4/1996 | Yamanaka | |
| 5,573,510 A | 12/1996 | Isaacson | |
| 5,685,863 A | 11/1997 | Botich et al. | |
| 5,704,920 A | 1/1998 | Gyure | |
| 5,728,073 A | 3/1998 | Whisson | |
| D397,434 S | 5/1998 | Pike | |
| 5,779,679 A | 7/1998 | Shaw | |
| 5,795,339 A | 8/1998 | Erskine | |
| 5,830,152 A | 11/1998 | Tao | |
| 5,957,887 A | 9/1999 | Osterlind et al. | |
| 5,964,731 A * | 10/1999 | Kovelman | 604/110 |
| 6,039,713 A | 3/2000 | Botich et al. | |
| 6,063,040 A | 5/2000 | Owen et al. | |
| D439,975 S | 4/2001 | Wilkinson et al. | |
| 6,210,371 B1 | 4/2001 | Shaw | |
| D445,495 S | 7/2001 | Schaefer et al. | |
| 6,277,102 B1 | 8/2001 | Carilli | |
| 6,468,250 B2 | 10/2002 | Yang | |
| 6,500,153 B1 | 12/2002 | Sheppard et al. | |
| D484,239 S | 12/2003 | Anderson | |
| D484,976 S | 1/2004 | Wilkinson | |
| 6,808,512 B1 | 10/2004 | Lin et al. | |
| D505,200 S | 5/2005 | Simpson et al. | |
| D506,549 S | 6/2005 | Woods | |
| 6,974,423 B2 | 12/2005 | Zurcher | |
| 7,351,224 B1 | 4/2008 | Shaw | |
| RE40,755 E | 6/2009 | McWethy et al. | |
| D601,243 S | 9/2009 | Bierman et al. | |
| D604,839 S | 11/2009 | Crawford et al. | |
| D613,398 S | 4/2010 | Crawford et al. | |
| D616,985 S | 6/2010 | Ade et al. | |
| D617,454 S | 6/2010 | Shaw | |
| D617,893 S | 6/2010 | Bierman et al. | |
| D627,065 S | 11/2010 | Ade et al. | |
| D645,962 S | 9/2011 | Shaw et al. | |
| D651,308 S | 12/2011 | Crawford et al. | |
| D657,462 S | 4/2012 | Siroky | |
| D657,867 S | 4/2012 | Effenberger | |
| D660,420 S | 5/2012 | Shaw et al. | |
| D663,833 S | 7/2012 | Ahn et al. | |
| 8,292,852 B2 | 10/2012 | Mulholland | |
| 8,343,094 B2 | 1/2013 | Shaw | |
| 8,366,682 B2 | 2/2013 | Wyrick | |
| 8,469,927 B2 | 6/2013 | Shaw et al. | |
| 8,496,600 B2 | 7/2013 | Shaw et al. | |
| 8,500,690 B2 | 8/2013 | Crawford | |
| 2001/0021827 A1 | 9/2001 | Ferguson et al. | |
| 2002/0068907 A1 | 6/2002 | Dysarz | |
| 2002/0082560 A1 | 6/2002 | Yang | |
| 2003/0181871 A1 | 3/2003 | Wilkinson et al. | |
| 2003/0078540 A1 | 4/2003 | Saulenas et al. | |
| 2003/0236504 A1 | 12/2003 | Chen | |
| 2004/0015135 A1 | 1/2004 | Wilkinson | |
| 2004/0019329 A1 | 1/2004 | Erskine | |
| 2004/0133172 A1 | 7/2004 | Wilkinson | |
| 2004/0204688 A1 | 10/2004 | Lin et al. | |
| 2005/0004524 A1 | 1/2005 | Newby et al. | |
| 2005/0288607 A1 | 12/2005 | Konrad | |
| 2006/0129122 A1 | 6/2006 | Wyrick | |
| 2006/0155244 A1 | 7/2006 | Popov | |
| 2006/0189934 A1 | 8/2006 | Kuracina et al. | |
| 2006/0235354 A1 | 10/2006 | Kaal et al. | |
| 2007/0260189 A1 | 11/2007 | Shaw et al. | |
| 2008/0132851 A1 | 6/2008 | Shaw et al. | |
| 2008/0132854 A1 | 6/2008 | Sharp | |
| 2008/0287881 A1 | 11/2008 | Kiehne | |
| 2008/0319345 A1 | 12/2008 | Swenson | |
| 2009/0198196 A1 | 8/2009 | West et al. | |
| 2009/0306601 A1 | 12/2009 | Shaw | |
| 2010/0000040 A1 | 1/2010 | Shaw et al. | |
| 2010/0003067 A1 | 1/2010 | Shaw et al. | |
| 2010/0241029 A1 | 3/2010 | Mahurkar | |
| 2010/0286604 A1 * | 11/2010 | Shaw | A61M 5/3234 604/68 |
| 2010/0317999 A1 | 12/2010 | Shaw et al. | |
| 2011/0264037 A1 | 10/2011 | Foshee et al. | |
| 2012/0022464 A1 | 1/2012 | Zivkovic et al. | |
| 2012/0071790 A1 | 3/2012 | Mahurkar | |
| 2012/0071827 A1 | 3/2012 | Zivkovic et al. | |
| 2012/0259243 A1 | 10/2012 | Shaw et al. | |
| 2012/0316466 A1 | 12/2012 | Crawford et al. | |

\* cited by examiner

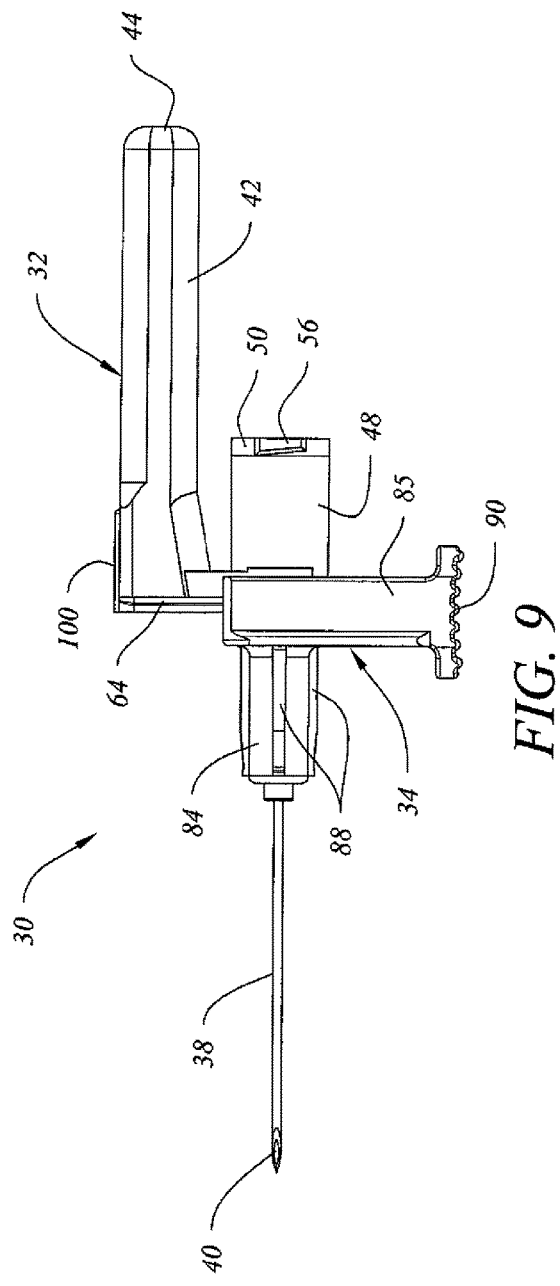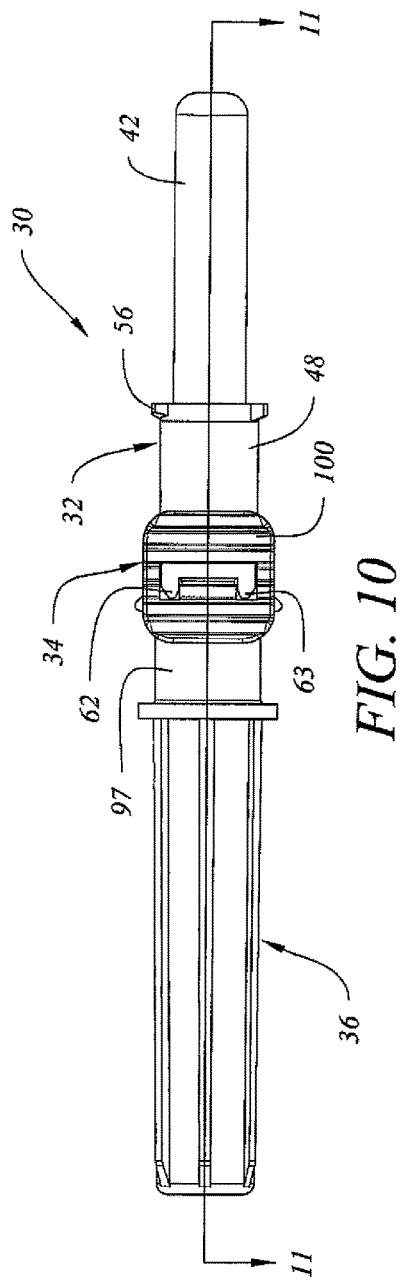
FIG. 9
FIG. 10

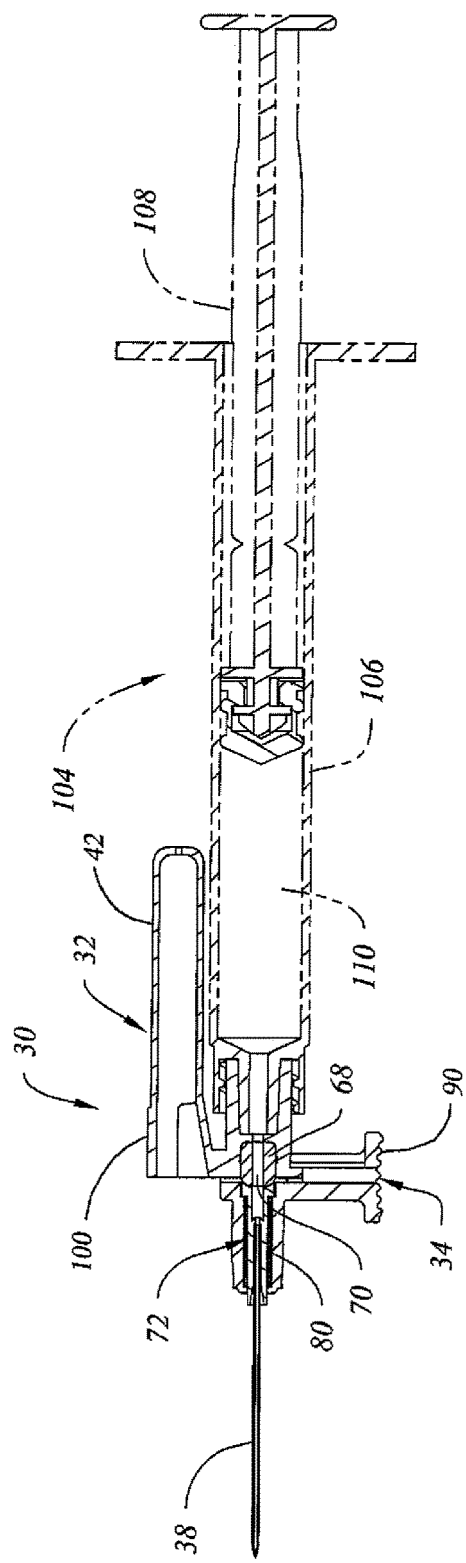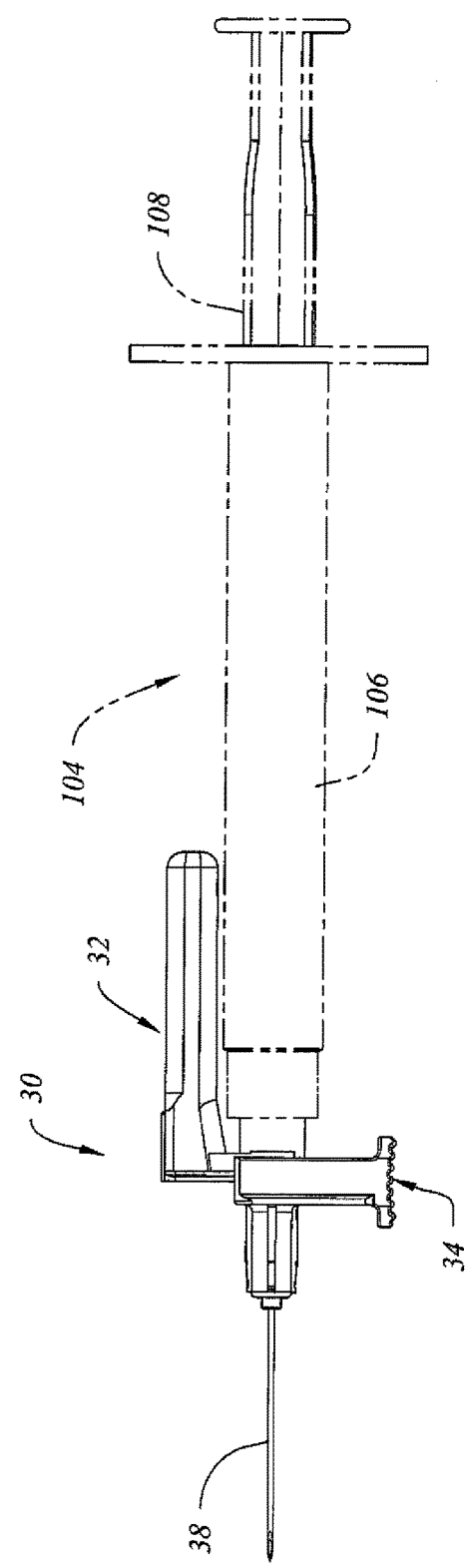
FIG. 13
FIG. 14

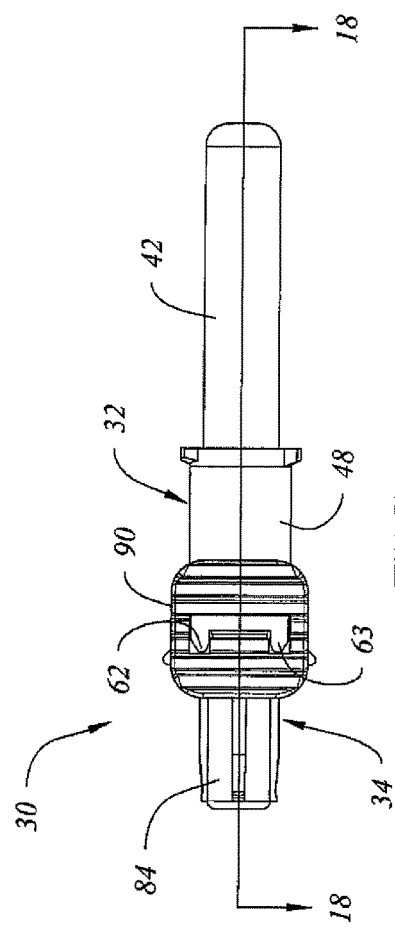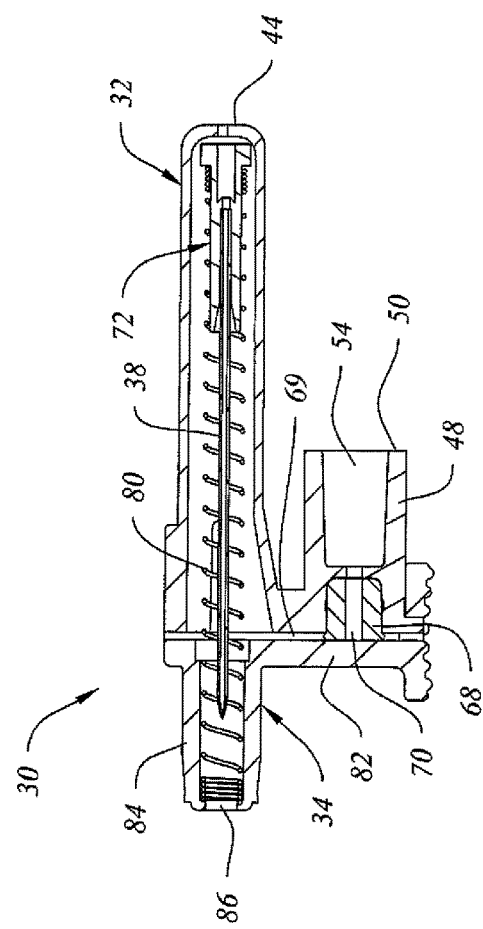

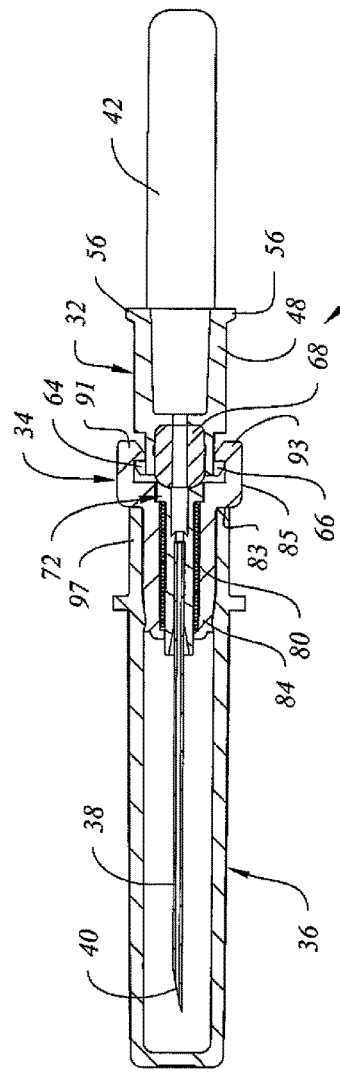
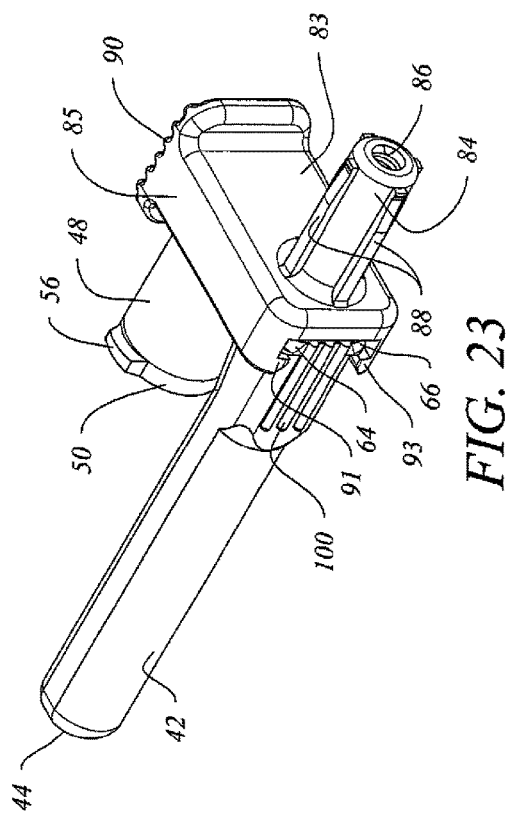
FIG. 22
FIG. 23

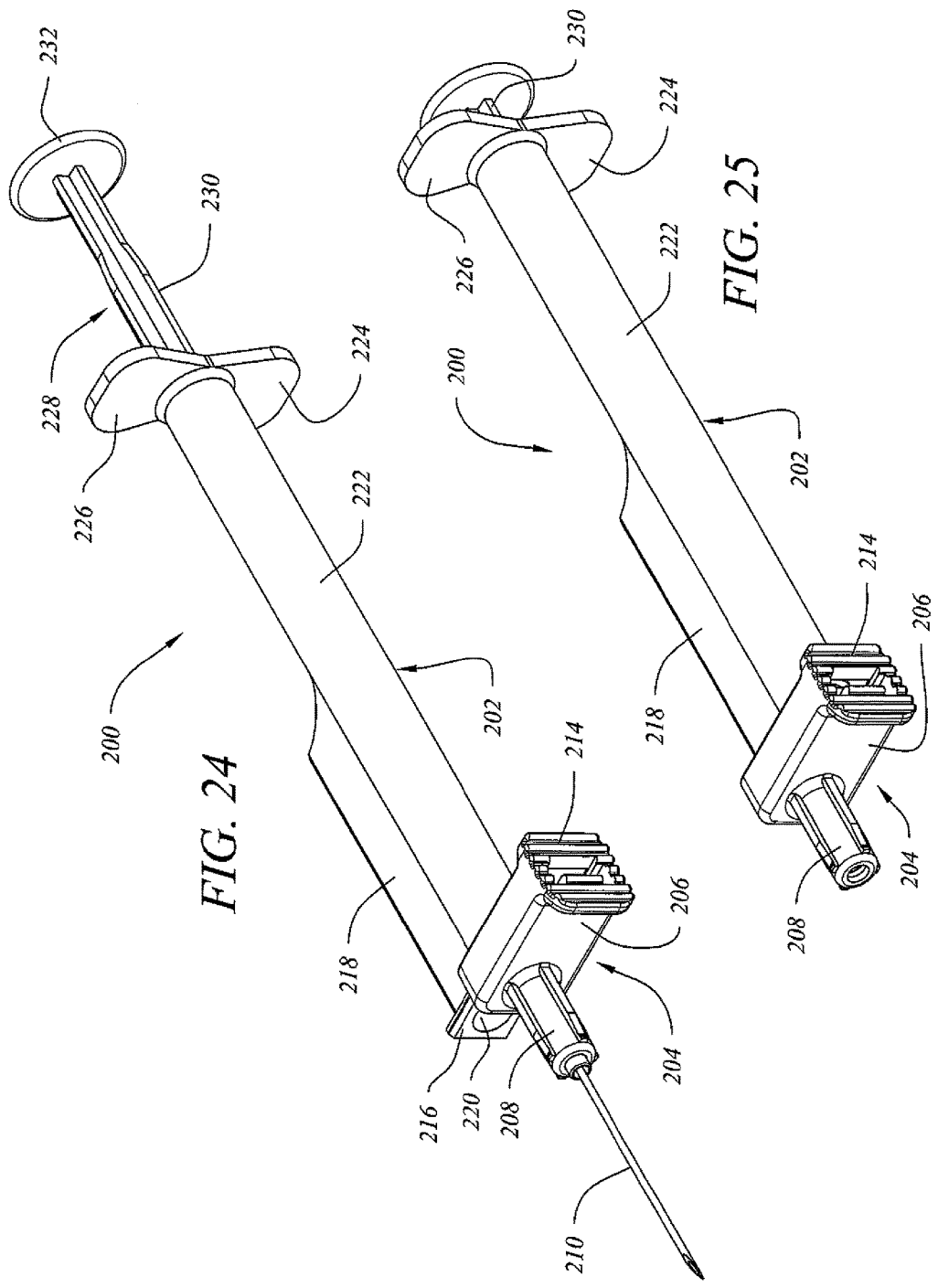

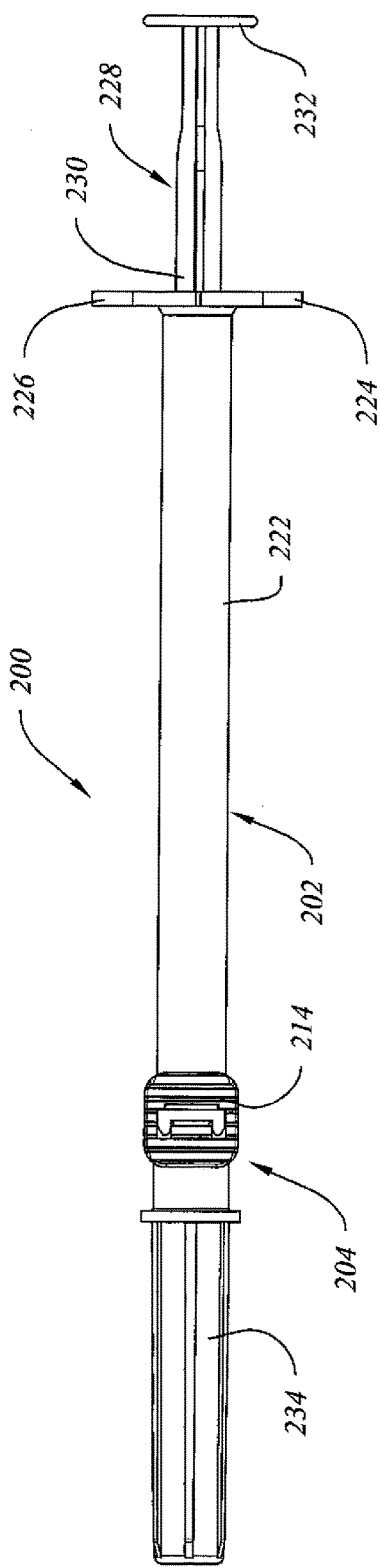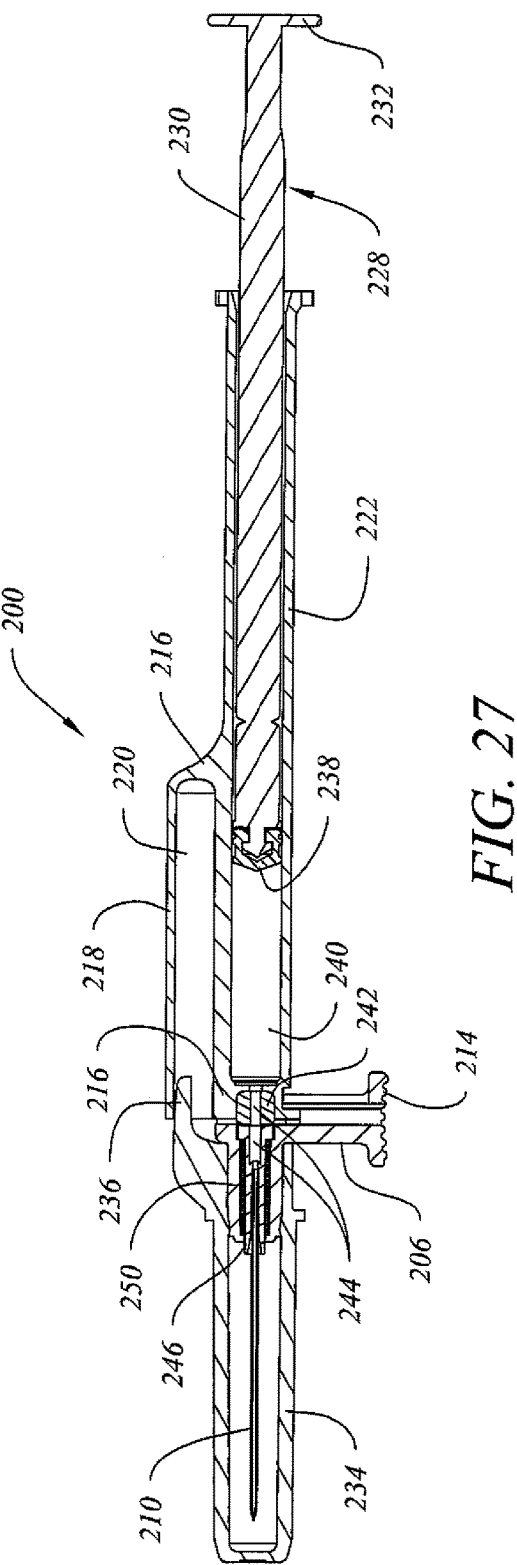
FIG. 26
FIG. 27

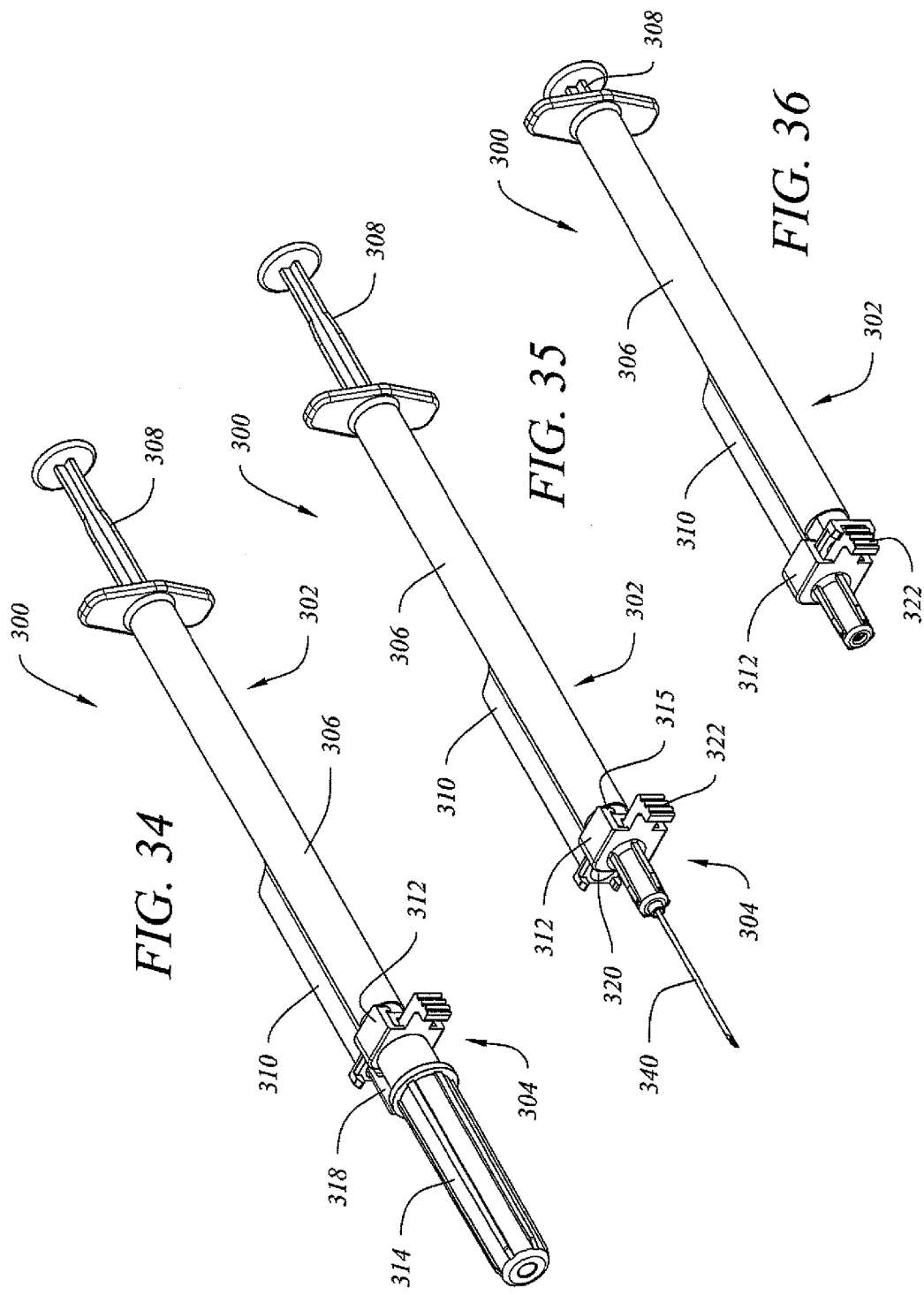

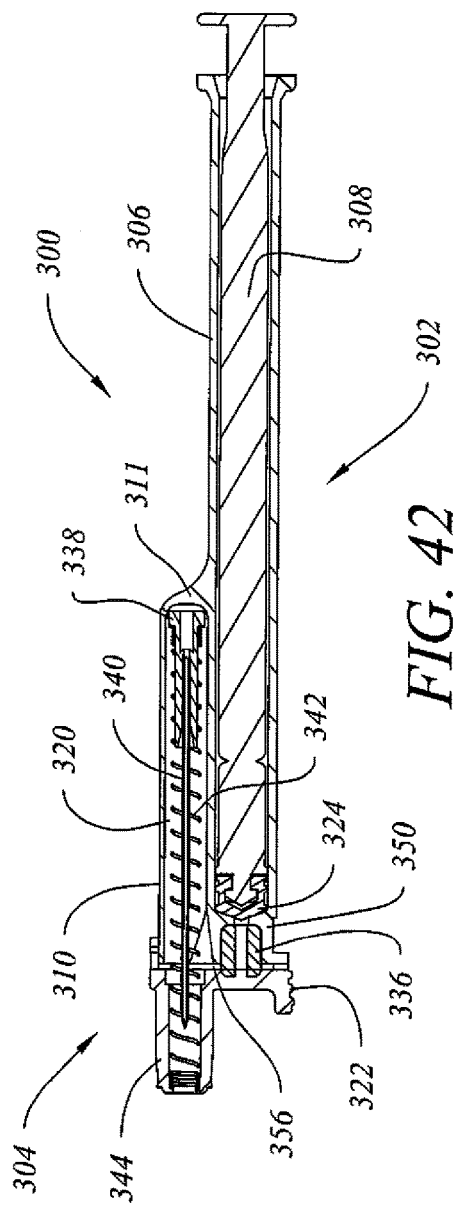
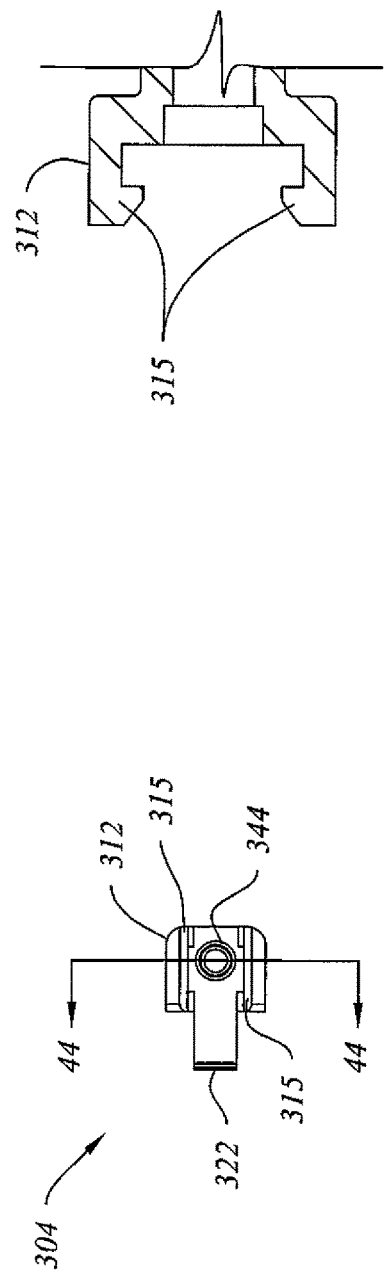
FIG. 42
FIG. 43
FIG. 44

COMBINED MEDICAL DEVICE WITH SLIDING FRONTAL ATTACHMENT AND RETRACTABLE NEEDLE

CROSS-REFERENCE TO RELATED APPLICATIONS

This application claims the benefit of the earlier filing dates of U.S. Provisional Patent Applications Nos. 61/737,263 filed Dec. 14, 2012, and 61/836,723 filed Jun. 19, 2013. This application is also a continuation-in-part of non-provisional U.S. patent application Ser. No. 13/714,819 filed Dec. 14, 2012, from which priority is claimed.

BACKGROUND OF THE INVENTION

1. Field of the Invention

This invention is a medical device having a frontal attachment comprising a retractable needle. One aspect of the invention relates to a frontal attachment that desirably clips onto and in sliding engagement with a connector housing comprising a unitarily molded or otherwise formed needle retraction cavity and at least a body or barrel portion of an associated medical apparatus in laterally spaced-apart relation to each other. The associated medical apparatus can include, for example, a syringe, IV-catheter insertion device, infusion set, fluid collection device, or other medical apparatus with which a retractable needle can be used.

Another aspect of the invention relates to a frontal attachment having a rearwardly biased retractable needle and a needle retraction mechanism, wherein the needle is aligned longitudinally with a fluid flow path through the connector housing to the associated apparatus whenever fluid is flowing through the needle but is not aligned with a needle retraction chamber until needle retraction is initiated.

Another aspect of the invention relates to a connector housing desirably comprising a needle retraction chamber open at one end and having a needle retraction cavity with a longitudinal axis that is substantially parallel to but laterally offset from the longitudinal axis or centerline of the needle during use and prior to needle retraction.

Another aspect of the invention relates to a connector housing that is desirably engaged with and slidable in relation to a frontal attachment in a direction substantially transverse to the longitudinal axis through a retractable needle seated in the frontal attachment. The slidable movement is desirably initiated by applying opposed forces to at least the frontal attachment and the connector housing. One of the oppositely directed forces can be a resistance force.

Another aspect of the invention relates to a medical device inside which a retractable needle holder and needle seated in a frontal attachment prior to use are biased into a safe position following use so that the needle tip is not exposed and the frontal attachment device cannot be reused. When the needle and needle holder are in the "safe position," the needle holder and a portion of the needle are desirably disposed in a retraction cavity inside a needle retraction chamber that is not coaxially aligned with the needle when fluid is passing through the needle during use of the medical device.

2. Description of Related Art

Conventional syringes comprising a generally cylindrical barrel, a needle projecting forwardly from the barrel, and a plunger slidably disposed inside the barrel through an opening in the rear of the barrel are well known. Some conventional syringes are made with a luer slip or luer lock connector on the front of the barrel to which a cooperatively configured changeable needle or needle hub is attachable to allow needles of different gauges or sizes to be used. The luer tips of such syringes are typically exposed to bacterial or viral contamination by incidental contact with a person or object during use. A notable exception is U.S. Pat. No. 8,343,094, which discloses a syringe that can be used with a changeable needle and also has a protective guard structure that extends forwardly past the luer tip to reduce the likelihood of contamination by contact.

More recently, syringes and other medical devices having fixed or changeable needles have been designed to embody various "safety" elements in an effort to control the spread of blood-borne pathogens and contamination by contact with exposed needles, bodily fluids or other contaminated objects or surfaces. Such devices sometimes include retractable needles, as in U.S. Pat. No. 7,351,224, but the term "safety" is also frequently applied to products having moveable guards, shields or covers that must be manipulated manually to cover or block access to the tip of a needle that is not retractable following use. Use of such moveable guards, shields or covers is not effective unless the needle is first removed from the patient or another device in relation to which fluid has been injected or extracted. The use of products having moveable guards, shields or covers as "safety" elements has in some cases been reported to increase the number of accidental needle-sticks, and such devices should be distinguished from those having retractable needles, and especially from those having needles that can be retracted while still inserted into a patient or other device. Examples of devices incorporating a "safety" element that is not a retractable needle are disclosed in U.S. Pat. No. 5,370,628 and U.S. Pat. No. 8,500,690. U.S. Pat. No. 8,500,690 acknowledges that the safety shield disclosed there cannot fully encompass the needle cannula until it is fully removed from the patient and also acknowledges that automatic shielding may be triggered by the intentional or unintentional release of the finger tabs by the user at any time following removal of the packaging cover.

In the previously known medical devices having retractable needles and needle retraction mechanisms, a needle retraction cavity is typically provided that is aligned with the longitudinal axis through the needle during use. In such devices a barrel and/or a cylindrical interior portion of a plunger handle often serve as the needle retraction cavity. An example of such a device is disclosed in U.S. Pat. No. 7,351,224.

In other medical devices, the needle retraction cavity is made as a unitary part of a body comprising both a barrel and a needle retraction cavity, each having a longitudinal axis that is substantially parallel to and spaced apart from the longitudinal axis of the other during use. In those devices, however, the needle and needle retraction cavity remain aligned during both use and needle retraction, and a crossover fluid pathway is provided between the barrel and the rear end of the needle. An example of such a device in which the needle is not rearwardly biased is disclosed in U.S. Pat. No. 4,941,883. An example of such a device in which the needle is rearwardly biased is disclosed in U.S. Pat. No. 6,468,250.

Among the medical devices having retractable needles, some have an actuator to which a retraction force is manually applied to retract the needle by sliding it rearwardly into a needle retraction cavity following use. Other devices either automatically retract the needle into a needle retraction cavity following use or require a separate and subsequently applied manual force to initiate needle retraction. The manual force needed to initiate needle retraction is sometimes applied longitudinally, such as through all or a portion of a plunger to reposition a plug or retainer member or to cut, fracture or pierce an interfering element. Such devices are disclosed, for example, in U.S. Pat. No. 5,503,010 and in U.S. Pub. No. 2008/0287881. Sometimes the initiating manual force is applied by pivoting a trigger element into an angular relationship with the longitudinal axis of the needle to reposition an element interfering with the retraction of a rearwardly biased element as shown, for example, in U.S. Pub. No. 2010/0317999. Sometimes the initiating force is applied by lateral movement of an actuator disposed inside a housing that comprises a needle retraction mechanism as disclosed, for example, in U.S. Pub. No. 2009/0306601. Sometimes the initiating force is applied by depressing a lever bar in a direction transverse to the longitudinal axis through the needle to pull a trigger pin and thereby release a slidable piston assembly biased rearwardly by a spring as disclosed, for example, in U.S. Pat. No. 4,973,316. A few known medical devices, as disclosed for example in U.S. Pat. No. 7,351,224, have needle retraction mechanisms with rearwardly biased needles that enable the needle to be retracted directly from the patient, but many others do not.

Another known medical device, disclosed in European Application No. EP 0 479 303 A1, is a frontal attachment for a luer tip syringe in which the frontal attachment comprises a needle retraction cavity having a longitudinal axis that is parallel to and spaced apart from the longitudinal axis of a connector portion to which a luer tip of the syringe is connected. With that device, however, the needle is coaxially aligned with the retraction cavity at all times and a fluid pathway is provided for fluid cross-over between the syringe and the needle. Also, even though the syringe with which the syringe can be used is characterized as "conventional" in the disclosure, the plunger portion of the syringe is specially adapted by the addition of a pushrod extending forwardly from the plunger seal that cooperates with the frontal attachment. Needle retraction in the device is initiated manually with an assist provided by a tensioned rubber band connected to the distal end of the retraction cavity.

Although the safety benefits of medical devices having retractable needles have become more widely recognized and appreciated in recent years, in the interest of safety for patients, their families and health care workers, a need remains for medical devices having an economical and reliable frontal attachment for use with medical apparatus such as a conventional syringe or IV-catheter introducer having a luer lock or luer slip connector. The needed devices should be usable without requiring special adaptation or modification of an associated medical apparatus (such as a syringe), have few parts, be comparatively inexpensive to manufacture, and embody a selectively attachable, retractable needle of a desired size and a needle retraction mechanism that can be activated with one hand and will retract the needle directly from a patient without applying a force during needle retraction.

SUMMARY OF THE INVENTION

The invention disclosed here is a medical device comprising a frontal attachment and a connector housing. The subject frontal attachment and the connector housing are desirably selectively attachable and are maintained in closely spaced, slidable relation to each other by one or more structural elements connected to one or both of them. In one embodiment of the invention, the frontal attachment desirably clips onto and slidably engages the connector housing, and a stop member is provided to prevent over-travel or disengagement. The connector housing also desirably comprises as an integral portion of the device at least part of an associated medical apparatus with which a retractable needle can be used. Such associated medical apparatus can include, for example, a syringe, IV-catheter insertion device, infusion set, or fluid collection device. The connector housing desirably further comprises a needle retraction chamber and a needle retraction cavity, both of which have a common longitudinal axis that is offset from and not aligned with the longitudinal axis of the needle during use of the medical device and prior to needle retraction.

In one embodiment of the invention, the frontal attachment comprises a body, a needle retraction assembly seated inside the body, and a forwardly projecting needle. The needle retraction assembly desirably includes a needle holder and a biasing member that biases the needle holder rearwardly in relation to the body. The forwardly projecting needle is desirably supported by the needle holder seated inside the body of the subject frontal attachment, and the needle holder is biased rearwardly. A satisfactory biasing member is a compressed coil spring that is held in compression when the body is attached to the connector housing, although other similarly effective biasing devices can also be used.

The connector housing desirably further comprises a needle retraction chamber having at least one unobstructed, forwardly facing, open end communicating with a rearwardly extending needle retraction cavity. If desired, a small vent can also be provided at or near the rear end of the needle retraction cavity. The connector housing is desirably unitarily molded together with at least a part of the associated medical apparatus, although other substantially rigid attachment means such as adhesives, plastic welding or the like can also be used to join a part of an associated medical apparatus, such as a syringe barrel, in a substantially fixed positional relationship to the needle retraction chamber of the connector housing. Whether the connector housing is unitarily molded together with or is otherwise attached to and made an integral part of at least a portion of the associated medical apparatus, the connector housing desirably establishes a substantially linear fluid flow path between the associated apparatus and the needle holder (without the need for cross-over channels or the like), thereby reducing the pressure required to move fluids from one to the other as compared to a non-linear flow path as might be experienced in a device having a cross-over channel between a fluid chamber and the retractable needle.

A fluid seal is desirably disposed between the frontal attachment and the connector portion of the connector housing, and is seated in a recess disposed in coaxial alignment with the connector portion of the connector housing in coaxial alignment with the needle prior to retraction. In one embodiment of the invention, the fluid seal is annular and is movable so that it remains aligned with the connector portion of the connector housing and is repositioned into facing contact with the rear of the body of the frontal attachment as needle retraction is initiated. The annular fluid seal desirably surrounds the fluid flow path between the connector housing the body of the frontal attachment prior to needle retraction and restricts fluid leakage between facing surfaces of the body and connector housing prior to, during and after needle retraction. The needle retraction cavity inside the needle retraction chamber of the connector housing is initially offset from the longitudinal axis through the needle but is desirably moved laterally into substantial alignment with the needle axis during needle retraction. A locking needle cap is desirably provided to prevent premature activation of the needle retraction mechanism during packaging, shipping and handling, and to protect the needle tip from being blunted, bent or otherwise damaged prior to use.

Needle retraction is desirably initiated by steadying or stabilizing the subject medical device relative to the patient and then applying pressure, desirably with one hand, to move the needle retraction cavity and the connector housing relative to the frontal attachment until the retraction cavity is substantially coaxially aligned with the longitudinal axis of the needle. As shown in one embodiment, an optional textured contact surface is disposed on at least one of the frontal attachment and the connector housing, respectively, to facilitate application of opposed or oppositely directed forces. Manual pressure is desirably applied in facing directions along an axis that is substantially parallel to a sliding interface between the frontal attachment and the connector housing, and substantially transverse to the laterally spaced longitudinal axes through the needle and the needle retraction chamber. As used herein, the term "sliding interface" refers to an interface that permits relative sliding movement between facing surfaces of the frontal attachment and the connector housing. It should be appreciated, however, that one of the oppositely directed forces applied to initiate needle retraction in the subject medical device can be a resistance force. Although not shown in the accompanying drawings, it will also be appreciated upon reading this disclosure that similarly effective but more complex apparatus can be substituted for the manual pressure used to initiate needle retraction. For example, one can incorporate into the subject medical device another biasing means such as a spring-activated or other similarly effective mechanism to reposition the needle retraction cavity into substantial coaxial alignment with the needle to facilitate needle retraction following use of the device. As will be apparent to those of ordinary skill in the art upon reading this disclosure, the use of such a biasing means will also require a release or triggering element to release the bias and thereby initiate relative sliding movement between the frontal attachment and the connector housing.

When the opening into the retraction cavity is sufficiently aligned with the head of the needle holder to receive the needle holder into the needle retraction cavity, a biasing member such as a compressed coil spring disposed in the body propels the needle holder and needle rearwardly, simultaneously withdrawing the beveled front tip of the needle so that it no longer projects forwardly from the body of the frontal attachment. As the needle retraction chamber slides laterally relative to the needle, the annular fluid seal reduces the likelihood of any fluid leakage from the subject medical device due to fluid flow out of the associated medical apparatus following use.

The subject medical device provides numerous benefits and advantages when compared to prior art devices. Once such benefit is that needle retraction can be activated independent of aspiration so that, for example, fluid can be withdrawn from a knee and the needle can still be retracted without fully depressing the plunger handle. Another benefit is that the subject medical device is configured to retract the needle directly from a patient without first having to manually withdraw the needle and risk possible contamination by exposure to bodily fluids containing infectious pathogens. Needle retraction can also be initiated following injection of a partial dose. Greater control can be exercised by the clinician using the invention because retraction is initiated by applying pressure closer to the base of the device, thereby reducing the likelihood of needle "wobble" in the patient.

In one embodiment of the invention, the subject medical device is also provided with a needle cap or needle cover that releasably engages the body and locks the connector housing into a position where it cannot be moved sufficiently to permit premature activation of the needle retraction mechanism without first removing the needle cap. If desired, the subject medical device can itself be used as a cover, closure or cap for a prefilled syringe. When made in combination with a syringe barrel, for example, the subject frontal attachment can be used to draw up a dose of expensive or caustic drugs or medicines and then capped for later use to avoid waste or injury. While the needle cap or cover is in place, the medical device of the invention can also be conveniently carried in a pocket or clipped inside of or onto it, particularly when configured as described below.

If desired, the subject medical device can be rigidly mounted to, integrally molded with, or otherwise manufactured or assembled as at least part of an associated medical apparatus. As one example, the connector housing and syringe barrel are unitarily or integrally molded from a moldable, medical grade polymeric resin. As another example, a syringe barrel is otherwise attached or connected in substantially fixed relation to the connector portion of the connector housing and is disposed in substantially coaxial alignment with the needle retraction assembly and the needle prior to movement of the connector housing relative to the frontal attachment following use but prior to needle retraction. In this embodiment, the substantially parallel, centrally disposed longitudinal axes through the needle retraction chamber and needle retraction cavity are still desirably spaced laterally apart from each other even if the needle retraction chamber and syringe barrel are unitarily or integrally molded in such manner that they are side by side with no open space between them so that part of the needle retraction chamber and part of the syringe barrel share a common wall. Several benefits can be achieved through use of this embodiment, and it can be packaged and sold in combination with a plunger and plunger seal that cooperate to create a variable volume fluid chamber inside the device that is aligned with the needle and enables the device to be used either to inject or withdraw fluids through the needle under either positive or negative pressure.

The frontal attachment of the invention can also be used with needles and syringes of different and varying gauges and sizes without special modification. If desired, either the associated medical apparatus with which the subject medical device is used, or the medical itself, can be provided with a plug containing an anticoagulant such as heparin to use in blood gas applications. The structure and operation of the invention are simplified by the provision of a substantially linear fluid flow path and a needle retraction chamber and associated retraction cavity that are offset laterally from the fluid flow path during fluid injection or extraction. The subject medical device has few parts, and those are easily and inexpensively molded.

The medical device of the invention also embodies safety features that are not typically available in many prior art devices. For example, the subject device is effectively "locked shut" against reactivation and reuse by the spring and needle that bridge the needle retraction cavity and body together following retraction. The sliding lateral movement and associated repositioning of the needle retraction cavity relative to the fluid flow path through the connector housing and the presence of a fluid seal between the body and connector housing cooperate to interrupt the fluid flow path and prevent fluid backflow from an associated medical apparatus following use. After the needle is retracted, the subject medical device can be removed from the associated medical apparatus and disposed of as with other needle covers. In circumstances where the associated medical apparatus is reusable, it can be autoclaved, sterilized or otherwise processed for possible reuse independently of the needle-containing component.

Other benefits and advantages of the subject medical devices will likewise become more apparent to those of ordinary skill in the art upon reading this disclosure in relation to the accompanying drawings.

BRIEF DESCRIPTION OF THE DRAWINGS

The apparatus of the invention is further described and explained in relation to the following drawings wherein:

FIG. 9 is a top plan view of the medical device of FIG. 1;

FIG. 10 is a right side elevation view of the medical device of FIG. 1;

FIG. 13 is a cross-sectional plan view of the medical device as in FIG. 11, but with the needle cover removed and the syringe plunger withdrawn to an aspirated position;

FIG. 14 is a top plan view as in FIG. 12, but with the needle cover removed and the syringe plunger withdrawn to an aspirated position;

FIG. 17 is a right side elevation view of the medical device of FIG. 16;

FIG. 18 is a top plan view of the medical device taken along line 18-18 of FIG. 17;

FIG. 22 is a cross-sectional side elevation view taken along line 22-22 of FIG. 6;

FIG. 23 is a left front perspective view of the medical device as in FIG. 4 but having the needle cover removed and following needle retraction;

FIG. 24 is a right front perspective view of another embodiment of the medical device of the invention wherein the associated medical apparatus is a syringe having a body portion that is integrally molded as part of the connector housing and wherein the removable needle cover as depicted in relation to the embodiment disclosed above is not shown;

FIG. 25. is a right front perspective view as in FIG. 24 wherein a plunger handle of the associated medical apparatus is fully depressed and the needle is retracted;

FIG. 26 is a right side elevation view of the medical device as in FIG. 24 but with the needle cover shown;

FIG. 27 is a cross-sectional top plan view of the medical device as in FIG. 26;

FIG. 34 is a right front perspective view of another embodiment of the subject medical device in which a syringe barrel is molded together with the connector housing of the invention and showing a removable needle cover in place over the retractable needle and a plunger inserted into an opening at the rear of the syringe barrel;

FIG. 35 is the medical device of FIG. 34 with the needle cover removed and the retractable needle projecting forwardly from the frontal attachment in the use position;

FIG. 36 is the medical device of FIG. 35 with the plunger handle more fully depressed inside the syringe barrel and with the needle retraction chamber and needle retraction cavity moved laterally with respect to the frontal attachment and needle retracted;

FIG. 42 is a cross-sectional top plan view of the medical device of FIG. 41;

FIG. 43 is a rear elevation view of the frontal attachment of the medical device of FIG. 37; and FIG. 44 is a cross-sectional view taken along line 44-44 of FIG. 43, with portions broken away to simplify the view and better illustrate the resilient polymeric clips used to slidably engage the frontal attachment to the base of the connector housing.

DESCRIPTION OF PREFERRED EMBODIMENTS

Figure 1:
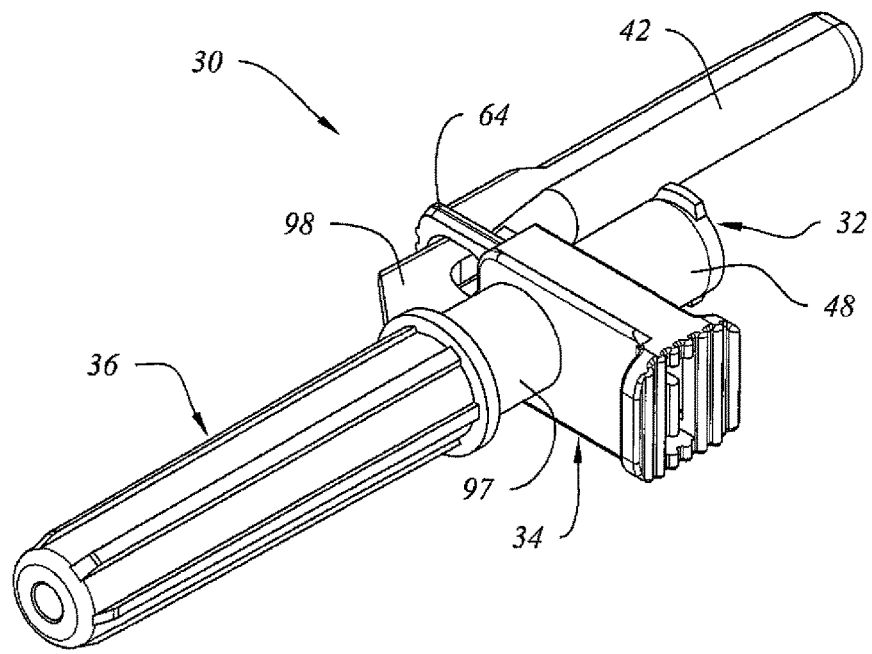
FIG. 1 is a right front perspective view of an embodiment of the medical device of the invention with the needle cover installed.
Figure 2:
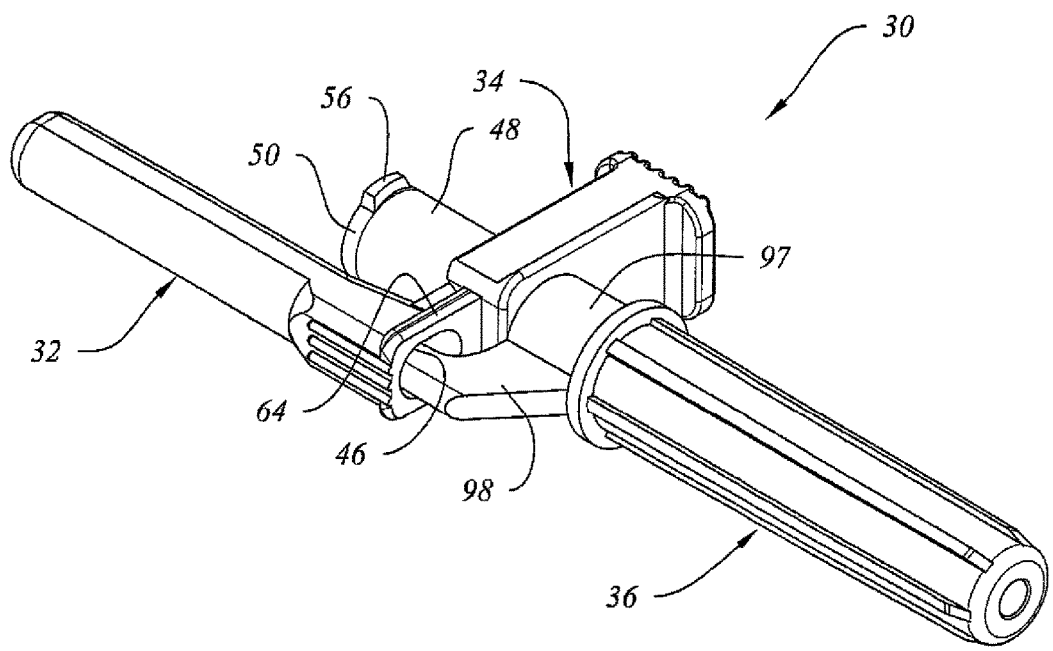
FIG. 2 is a left front perspective view of the medical device of FIG. 1.
Figure 3:
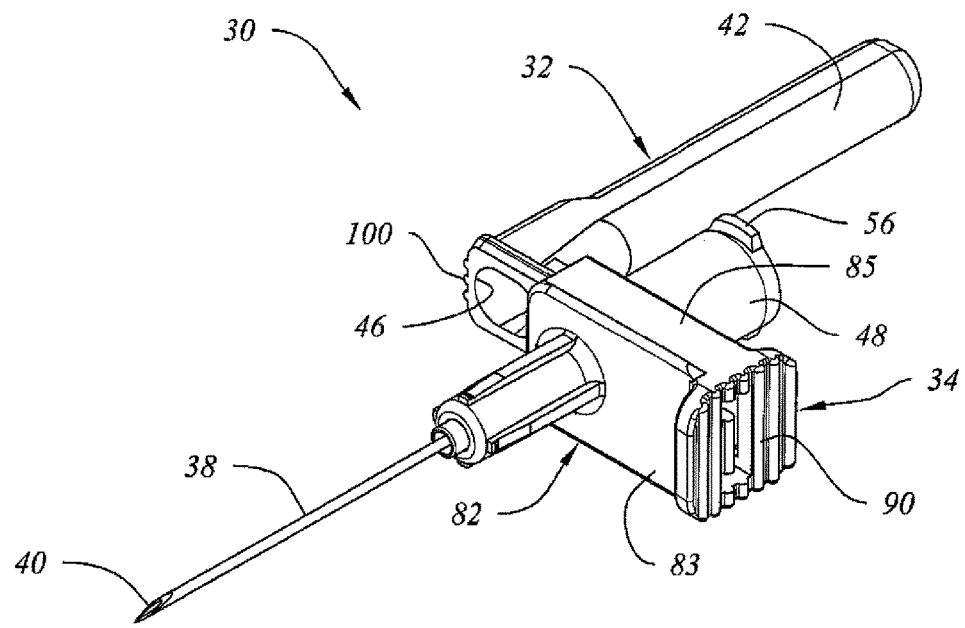
FIG. 3 is the medical device as in FIG. 1 with the needle cover removed.
Figure 4:
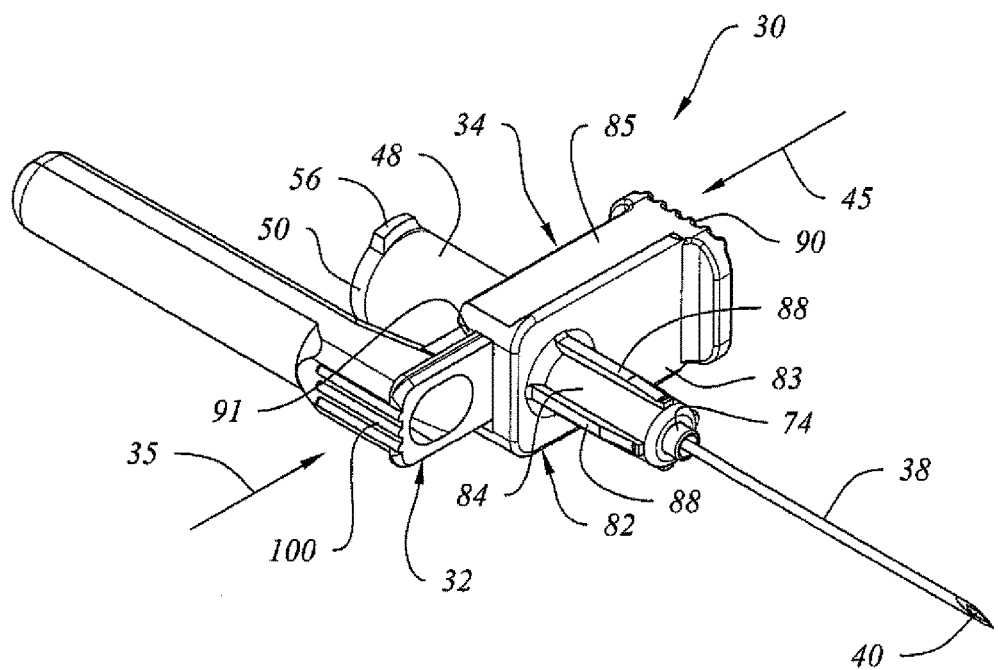
FIG. 4 is the medical device as in FIG. 2 with the needle cover removed and prior to needle retraction.
Figure 5:
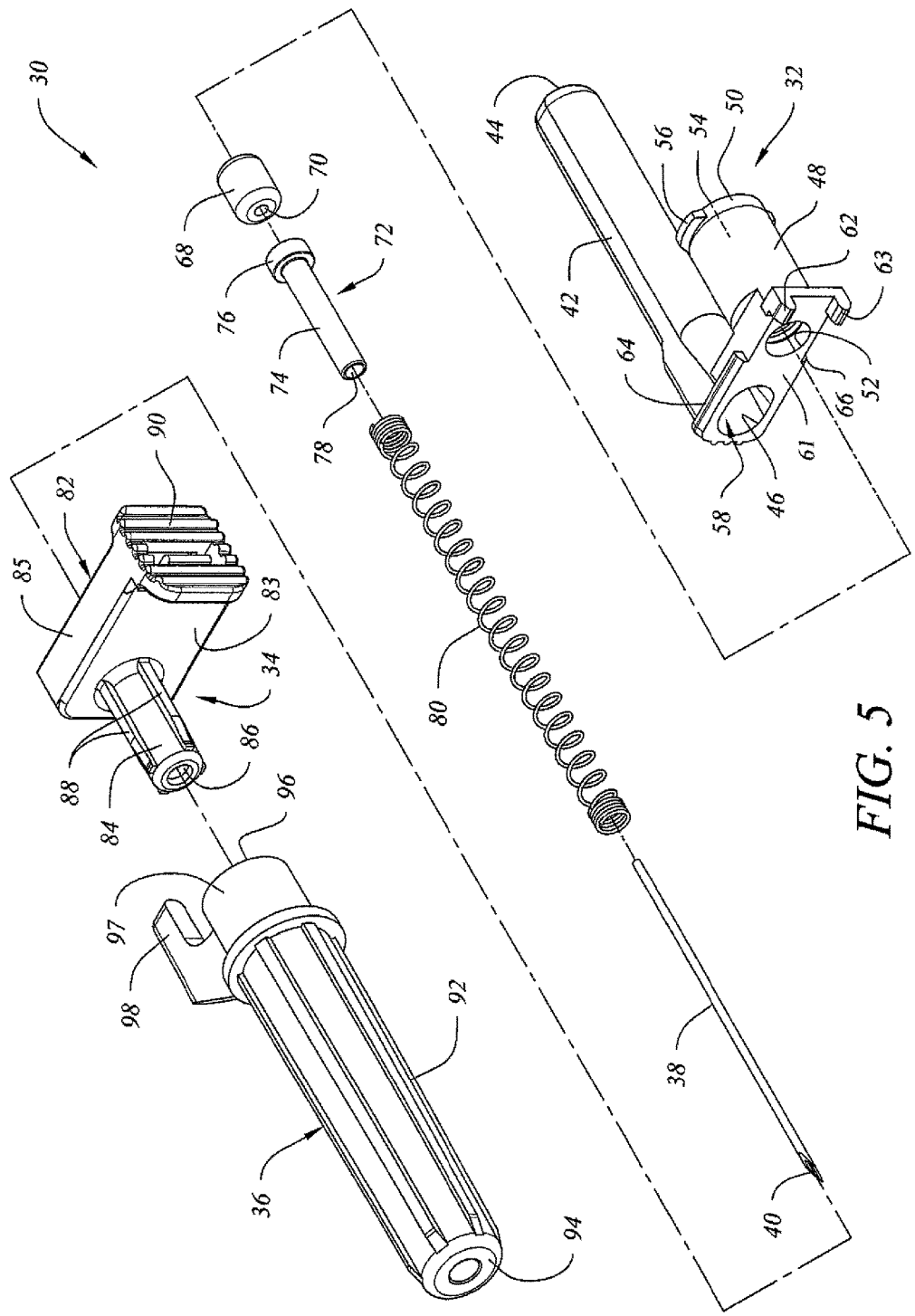
FIG. 5 is an exploded front perspective view of the medical device as in FIG. 1 (exploded along the longitudinal axis through the retractable needle assembly of the frontal attachment and the connector portion of the connector housing)

Referring to FIGS. 1, 2 and 10, medical device 30 comprises connector housing 32, frontal attachment 34 and locking needle cover 36. Referring to FIGS. 3, 4 and 9, locking needle cover 36 is removed to reveal needle 38 with upwardly facing beveled tip 40. Referring to FIGS. 5 and 9, connector housing 32 of medical device 30 desirably further comprises needle retraction chamber 42 having rearwardly facing closed end 44 and forwardly facing opening 46 bounding retraction cavity 58. Opening 46 is desirably elongated or oval shaped, with a transverse dimension greater than the inside diameter of the elongate cylindrical portion of needle retraction chamber 42. As seen in FIGS. 5-8, opening 46 desirably transitions along tapered inside wall 102 (back 103 visible in FIG. 8) to the inside diameter of needle retraction chamber 42. Tapered inside wall 102 facilitates insertion and removal of locking arm 98 of locking needle cover 36, and also facilitates the entry of needle holder 72 and retraction spring 80 into retraction cavity 58 during needle retraction, as is discussed in greater detail below. If desired, closed end 44 can also comprise a small opening (such as for venting purposes) provided that it is not large enough to permit the needle retraction spring 80, needle holder 72 or needle 38 from exiting through the rear of needle retraction chamber 42.

As depicted in FIG. 5, connector housing 32 desirably further comprises connector 48 for use in attaching medical device 30 to an associated medical apparatus such as, for example, syringe 104, which is shown and described in relation to medical device 30 in FIGS. 11-15. Connector 48 comprises a substantially cylindrical sidewall having an internal fluid flow path 54 with forwardly facing opening 52 and rearwardly facing open end 50. Two diametrically disposed, radially projecting luer locking tabs 56 are provided near rear end 50 for use in attaching connector 48 to an associated medical apparatus. Forwardly facing opening 52 desirably further comprises a recessed annular seating surface for receiving fluid seal 68. Fluid seal 68 also desirably comprises a centrally disposed fluid flow path 70 that is coaxial with fluid flow path 54 through connector 48. Referring to FIGS. 4 and 6-10, a textured digital contact surface 100 is desirably but optionally provided on the outwardly facing surface of needle retraction cavity 42 to facilitate the application of manual force (indicated by arrow 35 in FIG. 4) to connector housing 32 for use when initiating needle retraction, as discussed below.

Figure 20:
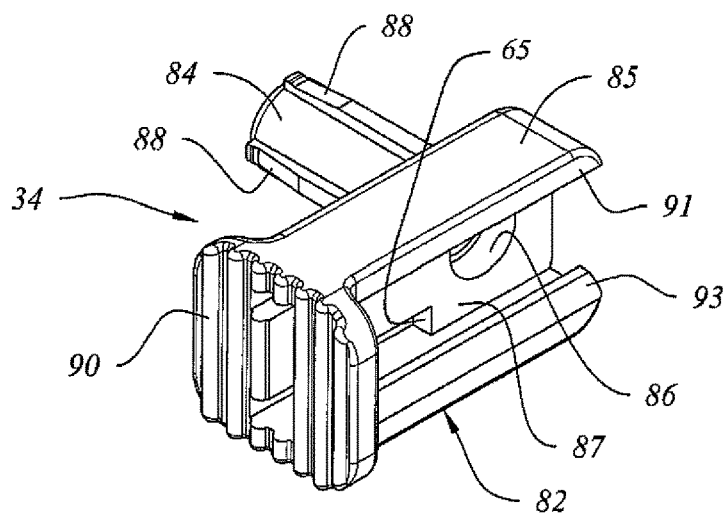
FIG. 20 is a left rear perspective view of the body portion of the frontal attachment.
Figure 21:
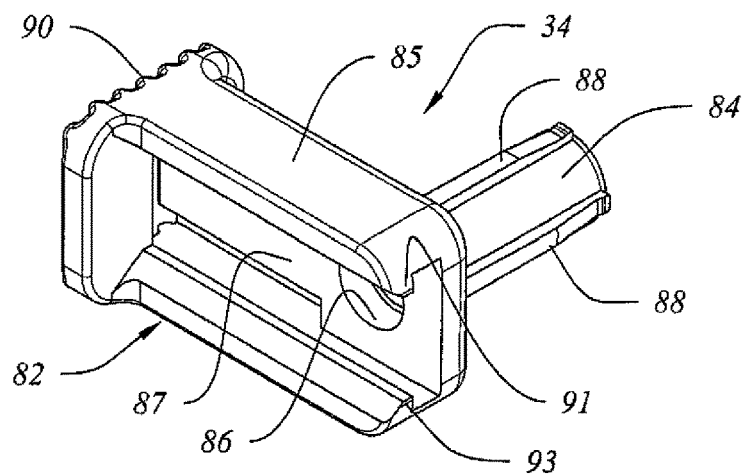
FIG. 21 is a right rear perspective view of the body portion of the frontal attachment.

Still referring to FIG. 5, frontal attachment 34 of medical device 30 further comprises a base 82 and forwardly projecting needle support 84. Needle support 84 preferably has a plurality of spaced-apart, tapered ribs 88 to provide releasable frictional engagement with the inside of collar 97 of locking needle cover 36, although it will be appreciated by those of ordinary skill in the art upon reading this disclosure that other similarly effective means can be provided for releasably securing locking needle cover 36 to needle support 84. Referring to FIGS. 5 and 20-22, base 82 and needle support 84 desirably comprises a stepped internal bore 86. Referring more particularly to FIGS. 20-21, base 82 further comprises rearwardly facing surface 87 with an opening into stepped internal bore 86 that desirably comprises an annular recess configured to receive and seat the larger diameter head portion 76 of needle holder 72 (visible in FIG. 5) when needle retraction mechanism (FIG. 5) comprising compressed spring 80 and needle holder 72 is inserted into frontal attachment 34 prior to the attachment of frontal attachment 34 to connector housing 32. An outwardly facing, textured contact surface 90 is desirably but optionally provided at the end of base 82 for use in applying a force as indicated by arrow 45 in FIG. 4 during needle retraction, as discussed in greater detail below. The force applied to frontal attachment 34 can be a resistance force, and preferably comprises a major component that is opposed or oppositely directed relative to the force applied as indicated by arrow 35 in relation to connector housing 34.

Referring generally to FIGS. 1-23 and more specifically to FIGS. 5-8 and 19-23, during assembly of medical device 30, the forward end of coil spring 80 is desirably inserted into and seated inside bore 86, and elongate tubular shaft portion 74 of needle holder 72 is desirably inserted into coil spring 80 and forced downwardly to compress the spring and allow the larger diameter head 76 of needle holder 72 to be seated inside bore 86. This causes compressed spring 80 to exert a rearwardly directed biasing force against the underside of head 76. Needle holder 72 desirably comprises a longitudinally extending bore 78 that is placed in fluid communication with needle 38 when needle 38 is installed inside the forwardly extending portion of bore 78. According to one embodiment of the invention, a shallow recess is provided in the rearwardly facing end of head 76 of needle holder 72 (not visible in FIG. 5) to releasably engage the forwardly facing end of fluid seal 68 when medical device 30 is assembled. As shown in FIGS. 3 and 4, the forwardly extending end of needle holder 72 desirably projects slightly beyond the forwardly extending tip of needle support 84 to facilitate the attachment of needle 38 to needle holder 72 following installation of the needle retraction mechanism and attachment of frontal attachment 34 to connector housing 32 by any suitable, conventional method known to those of skill in the art. Although needle 38 can be attached to needle holder 72 either before or after installation of needle holder 72 inside frontal attachment 34, attachment after installation of the needle retraction mechanism is preferred.

Following the insertion of fluid seal 68 into an annular recess inside forwardly facing opening 52 of connector housing 32 (as seen, for example, in FIGS. 5 and 22), and while holding needle holder 72 inside frontal attachment 34 against the rearwardly biasing force exerted by compressed spring 80, rearwardly facing surface 87 of base 82 of frontal attachment 34 is positioned opposite the forwardly facing surface 61 (seen in FIG. 5) of connector housing 32. Forwardly facing surface 61 of connector housing 32 is desirably configured to face and slidably engage the rear 87 of base 82, as opposed rails 64, 66 (FIGS. 5, 8 and 19-23) of connector housing cooperatively engage opposed rails 91, 93, respectively, of base 82. Rails 64, 66 and 91, 93 are desirably made so that they can snap into sliding engagement when connector housing 32 and frontal attachment 34 are held in facing parallel alignment so that bore 86 is disposed opposite opening 52 and squeezed together by applying force to the front of frontal attachment 34 and the back of connector housing 32 simultaneously. As frontal attachment 34 is attached to connector housing 32, fluid seal 68 is squeezed into abutting contact with the rearwardly facing end of head 76 of needle holder 72. Annular fluid seal 68 desirably prevents fluid leakage between connector housing 32 and frontal attachment 34 during use of medical device 30 and an associated medical device prior to repositioning connector housing 32 relative to frontal attachment 34 prior to needle retraction.

Referring to FIGS. 5, 17 and 20, stop members 62, 63 are desirably provided to engage in abutting contact with opposed upper and lower shoulders (lower shoulder 65 visible in FIG. 20) of rear surface 87 adjacent to base 82 of frontal attachment 34 to limit or restrict the range of lateral sliding motion of connector housing 32 relative to frontal attachment 34 to prevent accidental separation. When medical device 30 is assembled as described, head 76 of needle holder 72 (FIG. 5) is seated inside recess 86 (FIGS. 19-20) in frontal attachment 34, and a substantially linear fluid pathway is desirably defined through bore 54 of connector 48, bore 70 of fluid seal 68, bore 78 of needle holder 72, and needle 38.

Figure 6:
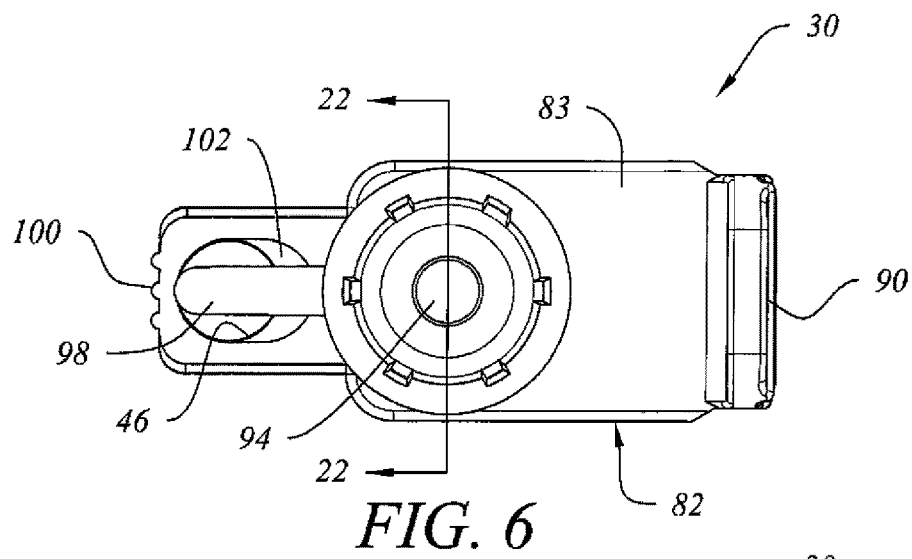
FIG. 6 is a front elevation view of the medical device of FIGS. 1 and 2.
Figure 7:
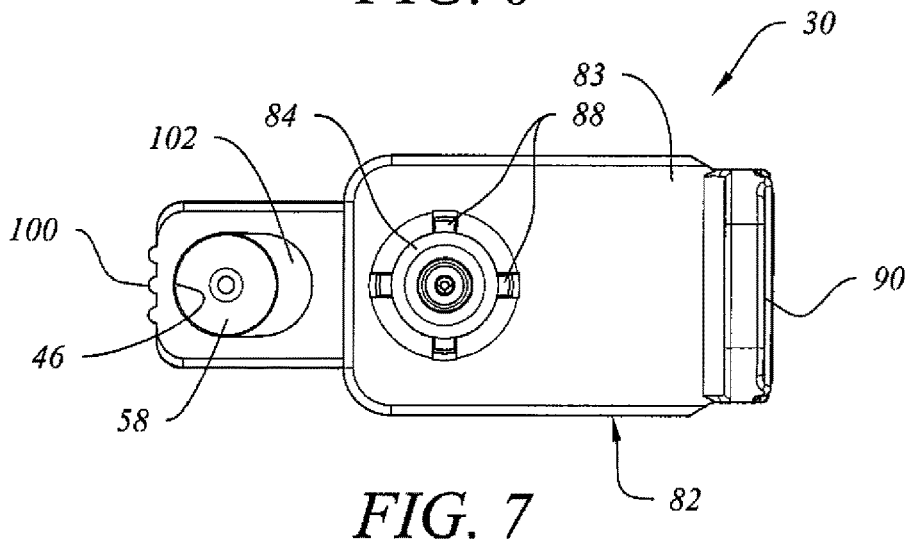
FIG. 7 is a front elevation view of the medical device of FIGS. 2 and 3, with the needle cover removed.
Figure 8:
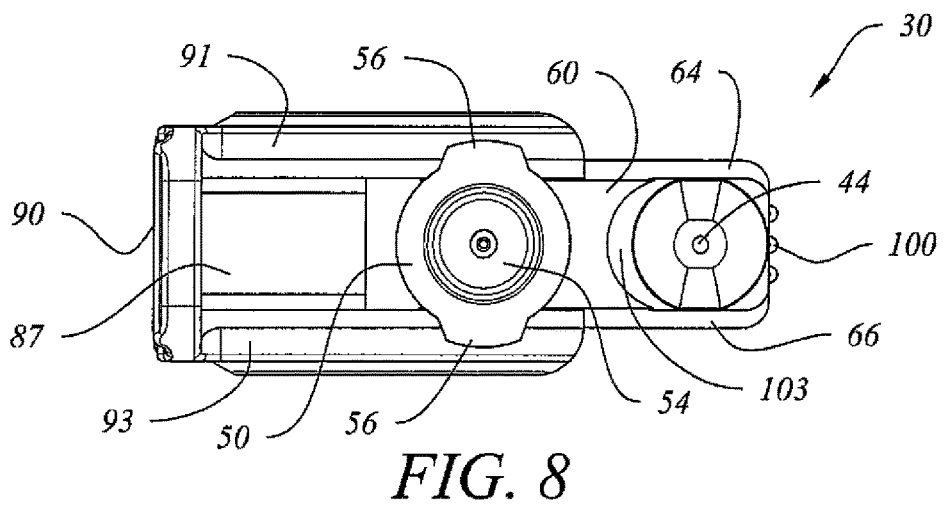
FIG. 8 is a rear elevation view of the medical device as in FIG. 7.

Referring to FIGS. 1-3, 5-6 and 11, locking needle cover 36 desirably comprises a substantially cylindrical sidewall 92 having closed end 94, open end 96, and a plurality of longitudinally extending, external reinforcing ribs to provide rigidity needled to protect needle 38 from damage prior to use. Locking arm 98 desirably projects rearwardly from collar 97 of locking needle cover 36 and is configured to be insert able into opening 46 of connector housing 32 to restrict relative sliding movement between connector housing 32 and frontal attachment 34 prior to removal of locking needle cover 36 from needle support 84. Other similarly effective locking structures can likewise be provided within the scope of the invention, and it will be appreciated that such locking structures are not required to be part of the needle cover. FIGS. 6 and 7, respectively, show medical device 30 as viewed from the front with and without locking needle cover 36 in place.

Figure 11:
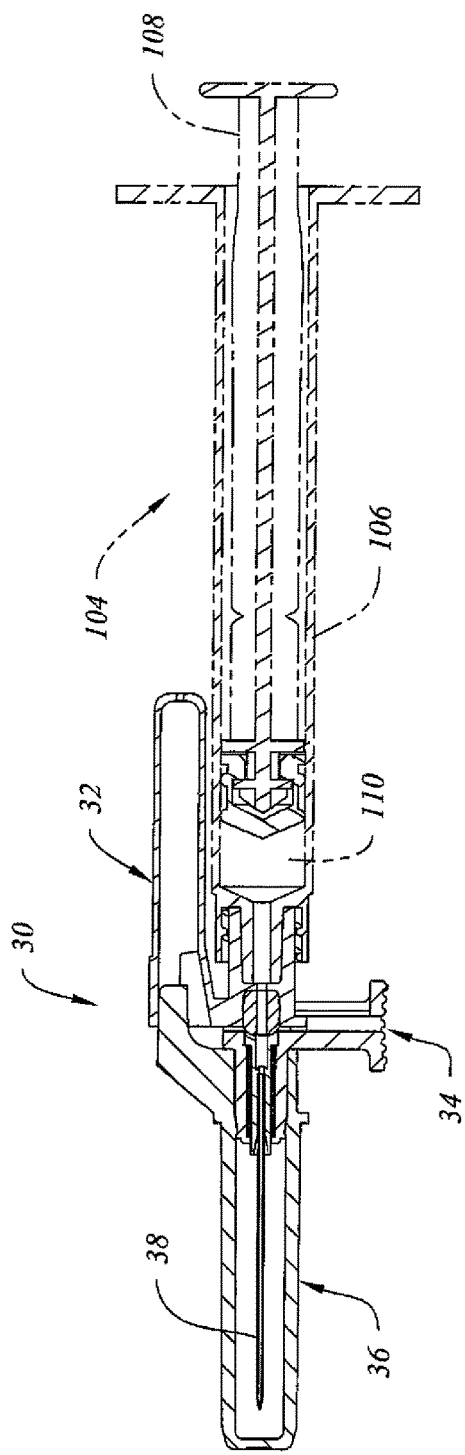
FIG. 11 is a cross-sectional plan view of the medical device in a pre-use position, taken along line 11-11 of FIG. 10, and also showing in phantom outline a conventional luer lock syringe attached to the connector housing of the subject medical device.
Figure 12:
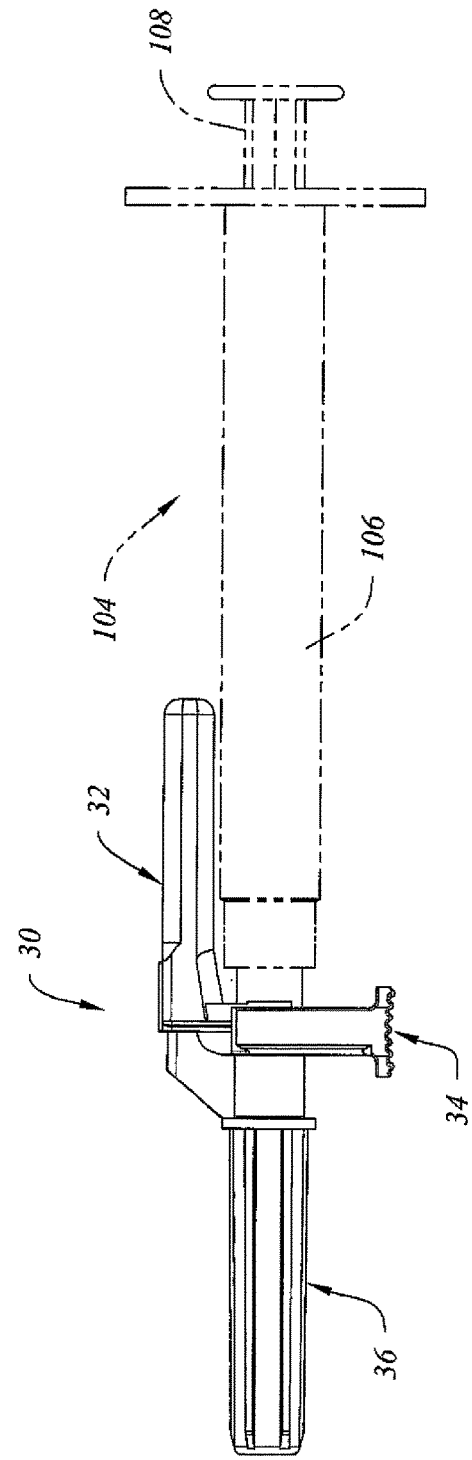
FIG. 12 is a top plan view of the medical device and syringe of FIG. 11, with the syringe again shown in phantom outline.

Referring to FIGS. 11-15, an associated medical apparatus is shown in phantom outline in combination with medical device 30 of the invention. The associated medical apparatus is a conventional syringe 104 having a generally cylindrical barrel 106 with a forwardly facing luer lock connector and a plunger 108 having a plunger seal slidably engaging the inside wall of barrel. Plunger 108 cooperates with barrel 106 to define a variable-volume fluid chamber 110 inside the syringe that can supply a fluid to needle 38 through the fluid pathway through medical device 30 as described above. As shown in FIGS. 11 and 12, medical device 30 and syringe 104 are depicted in fully assembled form with needle cover 36 in place over needle 38. Plunger 108 is shown in a position relative to barrel 106 that can be termed a "preinjection" position such as that in which a conventional syringe without a needle might be packaged and shipped prior to use.

Referring to FIGS. 13 and 14, the fully assembled medical apparatus of FIGS. 11 and 12 is shown again with the needle cover removed and with plunger 108 withdrawn to a position such as that in which fluid has been aspirated into fluid chamber 110. Such aspiration could occur, for example, by drawing fluid into the syringe from a vial or other fluid source, or by extracting a fluid sample from a patient (following expelling air from fluid chamber 110). For prefill use, syringe 104 can be filled to the desired level and packaged for shipment either with or without medical device 30 already in place.

Figure 15:
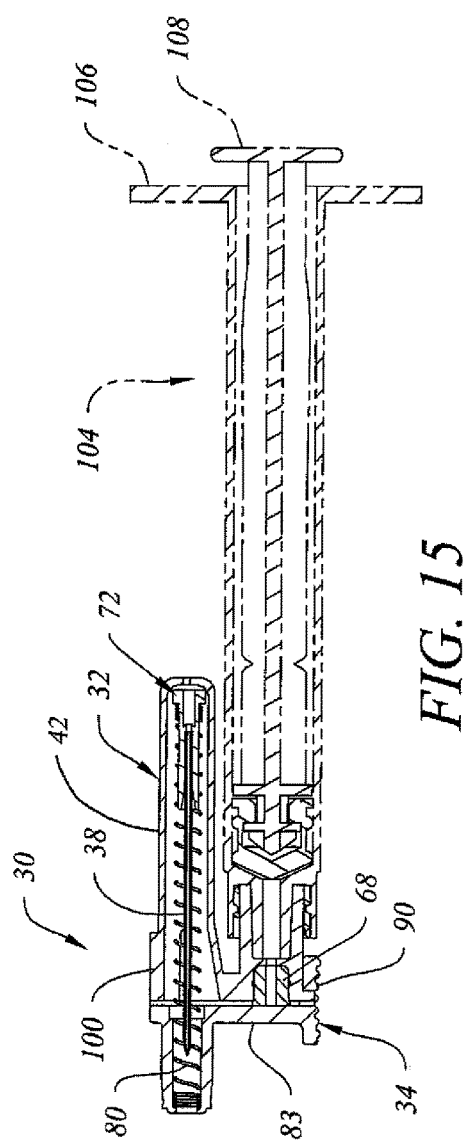
FIG. 15 is a top plan view as in FIG. 13, but with the syringe plunger fully depressed to a post-injection position and with the needle fully retracted.

Referring to FIGS. 13 and 15, following use of the fully assembled medical apparatus, needle retraction is desirably achieved in medical device 30 by repositioning connector housing 32 relative to frontal attachment 34 so that needle retraction chamber 42 is moved into coaxial alignment with needle 38. This can be done, for example, by manually applying pressure (as indicated by arrow 35 in FIG. 4) to optionally provided contact surface 100 of connector housing 32 while stabilizing barrel 106 and frontal attachment 34, and/or by applying resistance pressure (as indicated by arrow 45 in FIG. 4) to optionally provided contact surface 90 of frontal attachment 34. If needle 38 is not inserted in a patient at the time of needle retraction, frontal attachment 34 and connector housing 32 can be repositioned relative to each other by applying opposing manual pressure to contact surfaces 90 and 100 or to other portions of frontal attachment 34 and connector housing 32. The application of pressure as disclosed above will cause fluid seal 68 and connector housing 32 to move from a first position (FIG. 13 in which syringe 108 is aligned with needle 38 to a second position (FIG. 15) in which the needle retraction cavity of connector housing 32 is aligned with needle 38. As this repositioning occurs, the rearwardly directed biasing force of spring 80 will cause needle holder 72 and needle 38 to enter opening 46 when they are sufficiently aligned to permit full retraction. Similarly, if desired, medical device 30 can also be constructed by biasing connector housing 32 relative to frontal attachment 34 so that the biased repositioning to permit needle retraction occurs upon application of a triggering force to a cooperatively configured release element.

In FIG. 15, the fully assembled medical device of FIGS. 13 and 14 is shown again with plunger 108 fully depressed inside barrel 106 as it could be following an injection, with connector housing 32 repositioned relative to frontal attachment 34 from the position shown in FIG. 14 and with needle holder 72, spring 80 and needle 38 all retracted into medical device 30 in a safe position, with no part of needle 38 still projecting forwardly from frontal attachment 34. Following retraction, the expanded spring and the retracted needle can provide a "bridging" connection between frontal attachment 34 and connector housing 32 that will deter the removal of frontal attachment 34 from connector housing 32 to reconfigure medical device 30 to its pre-retraction state, and will also deter reverse movement of connector housing 32 relative to frontal attachment 34 that could otherwise realign a fluid pathway through medical device 30.

Figure 16:
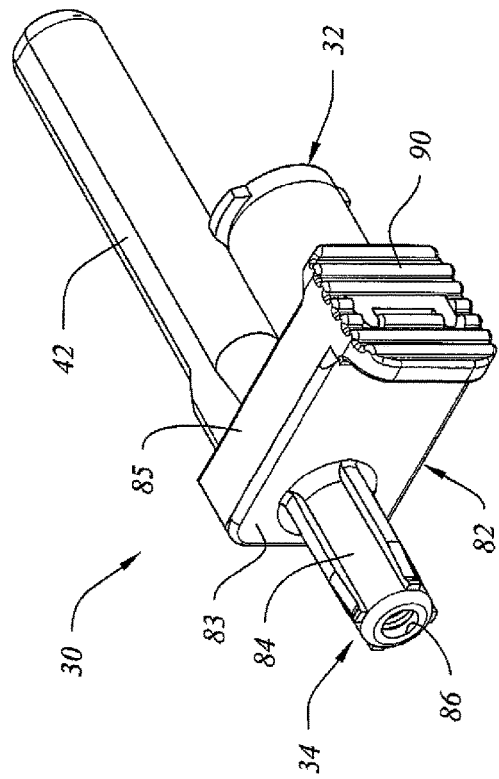
FIG. 16 is a right front perspective view of the subject medical device following detachment from a syringe and with the needle in the fully retracted position.
Figure 19:
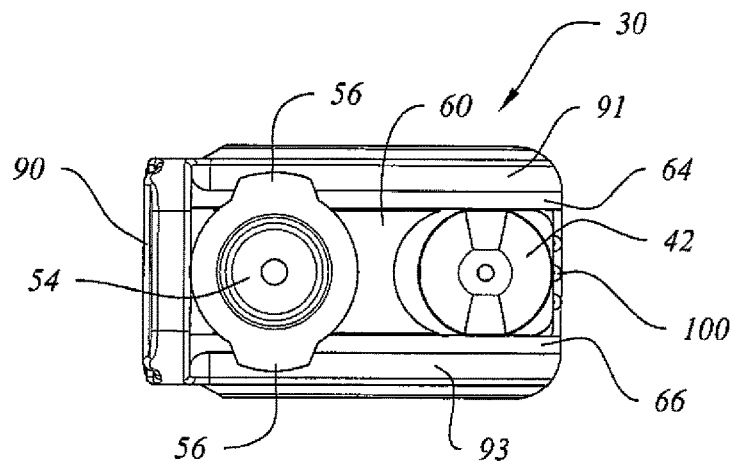
FIG. 19 is a rear elevation view of the medical device of FIG. 16.

In FIGS. 16-18, syringe 104 has been detached from medical device 30 by unscrewing the luer lock connector, and medical device 30 is ready for safe disposal. In FIG. 18, it is seen that fluid seal 68 remains in abutting contact with the back side of base 82 of frontal attachment 34 around bore 70 following needle retraction.

Connector housing 32, frontal attachment 34 and needle cover 36 of medical device 30 are all desirably made from any moldable polymeric material approved for such medical applications and for sterilization. Fluid seal 68 is desirably made of an elastomeric polymeric material having a composition and durometer that are satisfactory for containing fluids within the fluid pathway between connector housing 32 and frontal attachment 34 without degradation prior to and during use, and that will permit disengagement from needle holder 72 and relative sliding movement between connector housing 32 and frontal attachment 34 as seal 68 and needle retraction chamber 42 are repositioned laterally prior to needle retraction. Needle 38 is preferably made of stainless steel, another metal or alloy, or a ceramic or other material that is approved for such use. Compression springs are made of metal, are generally known in the industry, and are readily available from commercial vendors.

Another embodiment of the subject invention is disclosed in relation to FIGS. 24-33 of the accompanying drawings. Referring to FIGS. 24 and 25, a medical device 200 is disclosed in which an associated medical apparatus, in this case syringe barrel 222, is provided as a unitary part of the connector housing. Medical device 200 desirably comprises frontal attachment 204 and connector housing 202, which are selectively attached to each other and are maintained by one or more attachment members in closely spaced sliding relation to each other along at least one sliding interface allowing limited sliding lateral movement between frontal attachment 204 and connector housing 202 as previously discussed in relation to the embodiment of FIGS. 1-23. In FIG. 24, the needle cover (shown and described in relation to FIGS. 26-28 below) is removed to reveal needle 210.

Frontal attachment 204 desirably further comprises body 206, forwardly extending nose 208, retractable needle 210, and textured contact surface 214. Connector housing 202 further comprises base 216, needle retraction chamber 218, and syringe barrel 222. In FIG. 24, the needle cover (shown and described in relation to FIGS. 26-28 below) is removed to show a first position in which barrel 222 is coaxially aligned with needle support 208, laterally offset needle retraction chamber 218, and needle retraction cavity 220 having a forwardly facing opening that is unobstructed. In FIG. 25, connector housing 202 has been moved laterally relative to frontal attachment 204 to a second position in which needle retraction chamber 218 is substantially aligned with needle support 208, and needle 210 (no longer visible) has been retracted into needle support 208 and needle retraction cavity 220 (FIG. 24) inside needle retraction chamber 218.

In this embodiment of the invention, an associated medical apparatus such as syringe barrel 222 (or other associated medical apparatus previously mentioned in this disclosure) is rigidly connected to and part of the connector housing. In parts made with a moldable medical grade material, this substantially rigid connection can be achieved by any suitable method such as, for example, by unitarily or integrally molding connector housing 202 comprising base 216, needle retraction chamber 218 and syringe barrel 222 as a single unit, or by using other similarly effect known technologies including, without limitation, the use of laser welding or adhesives. When medical device 200 is configured in this manner, needle retraction cavity 220 is considered to be laterally spaced apart from barrel 222 even though needle retraction chamber 218 and barrel 222 share a common wall (seen better in FIG. 27). It will also be appreciated that medical devices of the invention having an attached associated medical apparatus can be made in which the needle retraction chamber and the associated medical apparatus do not share a common wall. Referring again to FIGS. 24 and 25, laterally projecting barrel flanges 224, 226 can also be integrally molded together as part of barrel 222 or can be separately fabricated and attached to the barrel by conventional methods. Plunger 228 is slidably disposed inside barrel 222 and is shown in FIG. 24 in a typical position relative to barrel 222 as it might be shipped and stored prior to use. As shown, plunger 228 comprises handle 230, end cap 232 and plunger seal 238 (visible in FIGS. 27-29). In FIG. 25, plunger handle 230 is more fully depressed relative to barrel 222 as it would be in an injection application. For other applications, such as withdrawal of a bodily fluid from a patient, the plunger handle can also be withdrawn a greater distance relative to barrel 222 than is shown in FIG. 24 when needle 210 is retracted.

Referring to FIG. 27, removable needle cover 234 is shown installed on medical device 220, with locking arm 236 projecting into needle retraction cavity 220 to limit relative sliding movement between body 206 of frontal attachment 204 (FIG. 26) and base 216 of connector housing 202 (FIG. 26) during shipment and handling prior to use. Without locking arm 236 or another similarly effective structure holding needle 210 in substantial coaxial alignment with fluid path 244 and fluid chamber 240 of barrel 222 prior to use, premature lateral shifting of frontal attachment 204 and/or connector housing 202 relative to the other could realign the retractable needle assembly comprising needle holder 246 and compressed needle retraction spring 250 with needle retraction cavity 220 sufficiently to allow spring 250 to expand and drive needle holder 246 and needle 210 rearwardly into needle retraction cavity 220.

Figure 28:
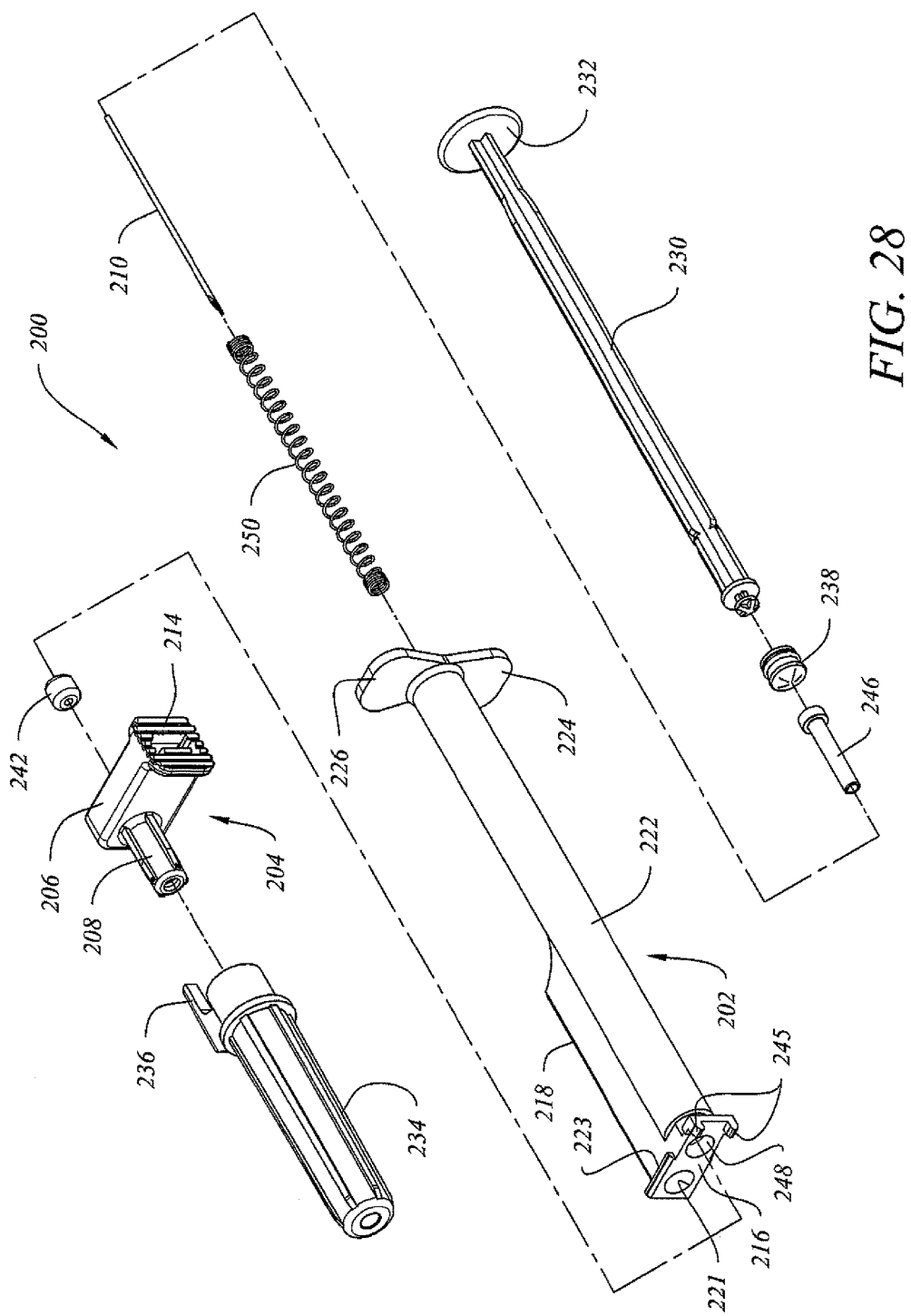
FIG. 28 is an exploded front perspective view of the medical device as in FIG. 26.

Referring to FIGS. 27-28, medical device 200 desirably further comprises annular plunger seal 238 disposed on the forwardly facing end of plunger handle 230 to provide sliding and sealing engagement with the inside wall of barrel 222 (FIG. 28). Referring to FIG. 28, connector housing 202 desirably further comprises laterally spaced-apart, forwardly facing openings 221 and 248. Opening 221 is provided to receive needle holder 246 and expanded needle retraction spring 250 during needle retraction following repositioning and realignment of connector housing 202 relative to frontal attachment 204. Upper and lower stop members 245 and upper and lower rails 223 (lower rail not visible) are desirably provided to facilitate assembly of frontal attachment 204 to connector housing 202, provide at least one lateral sliding interface between them that is substantially transverse to the longitudinal axis through needle 210 and barrel 222, and provide stop members and cooperatively aligned blocking structures that preclude accidental disassembly as described in greater detail above in relation to the first disclosed embodiment. In one embodiment, stop members 245 and the upper and lower rails 223 are cooperatively configured so that frontal attachment 204 can be snapped into sliding engagement with connector housing 202 and remain in sliding engagement with each other within a predetermined range of travel. The predetermined range of travel is desirably sufficient to permit movement between a first or initial position where needle 210 is aligned with barrel 222 and a second or subsequent position where needle 210 is aligned with needle retraction cavity 218.

Figure 29:
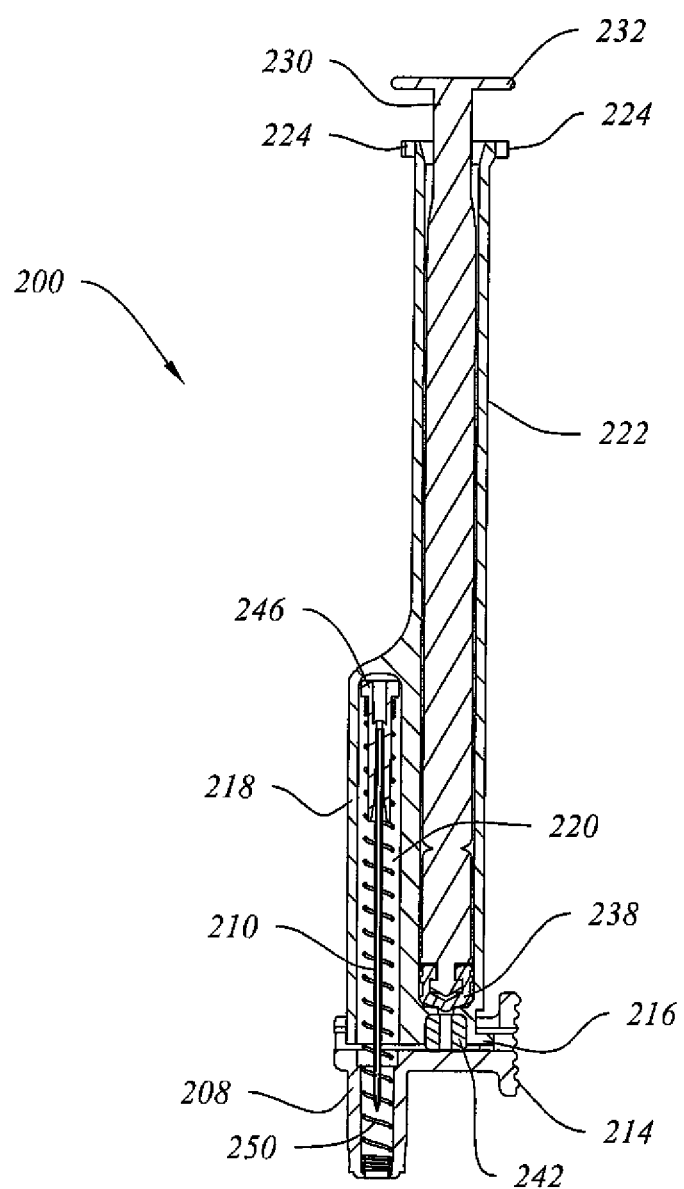
FIG. 29 is a cross-sectional top plan view taken along line 29-29 of FIG. 31 showing the needle in the post-retraction position.
Figure 30:
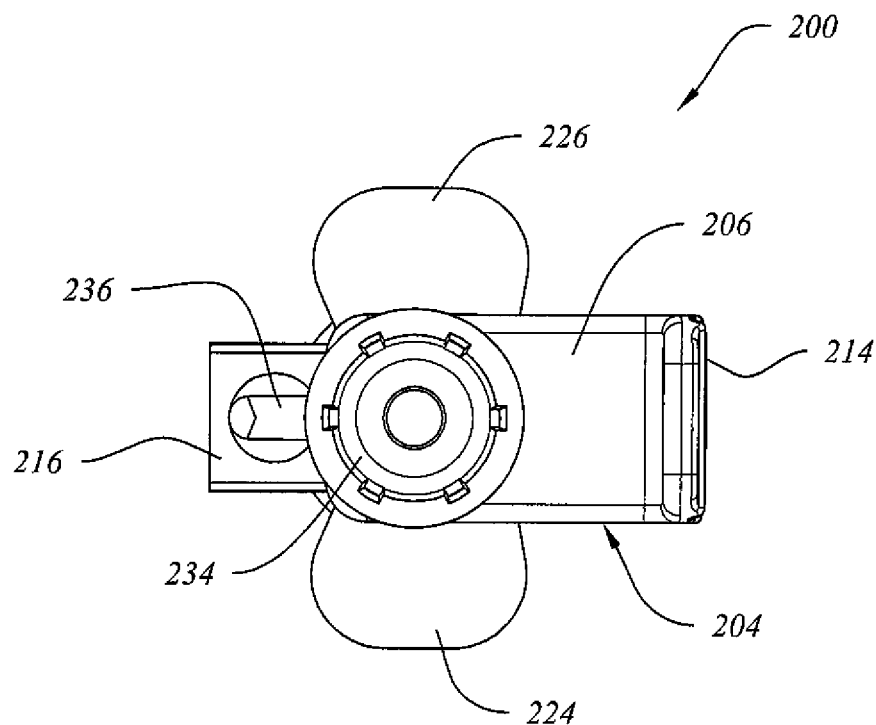
FIG. 30 is a front elevation view of the medical device of FIG. 26.
Figure 31:
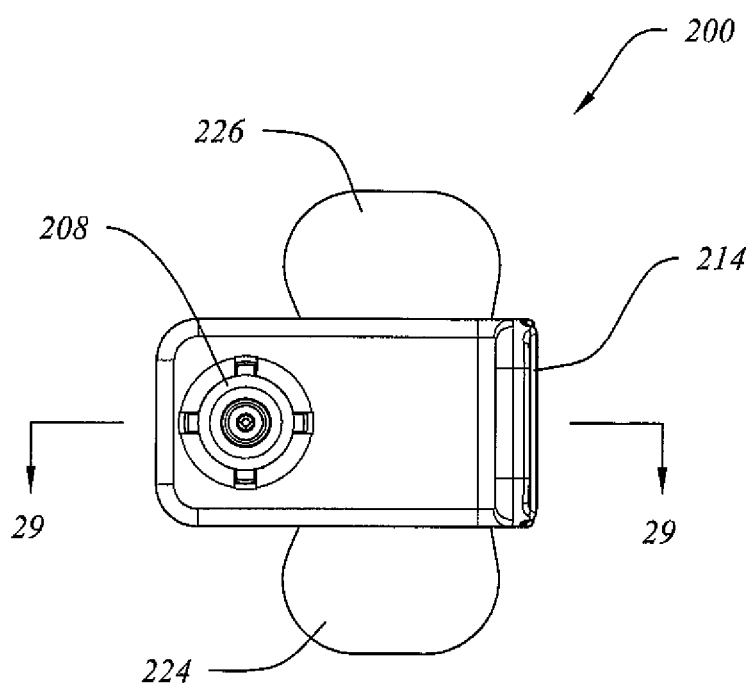
FIG. 31 is a front elevation view of the medical device of FIG. 26 following removal of the needle cover and also following needle retraction.
Figure 32:
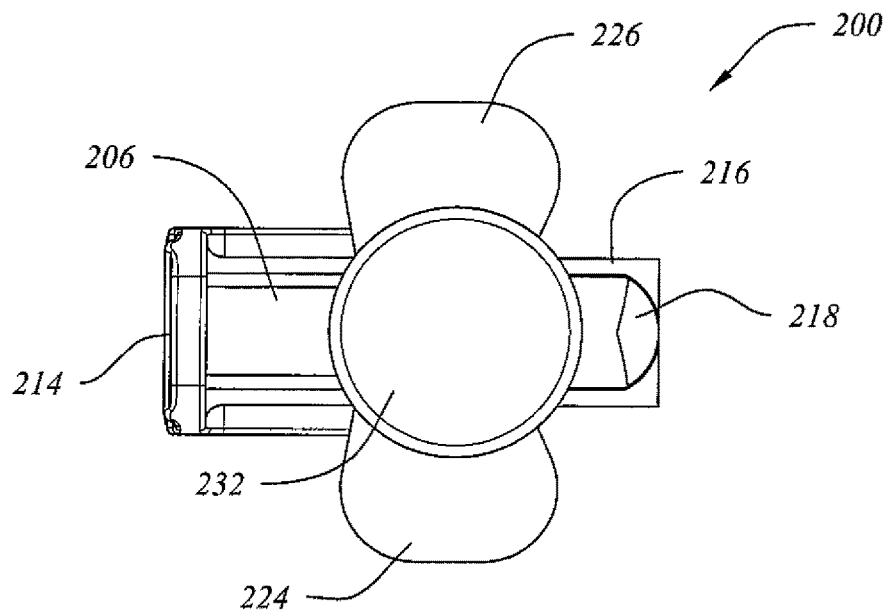
FIG. 32 is a rear elevation view of the medical device of FIG. 30.
Figure 33:
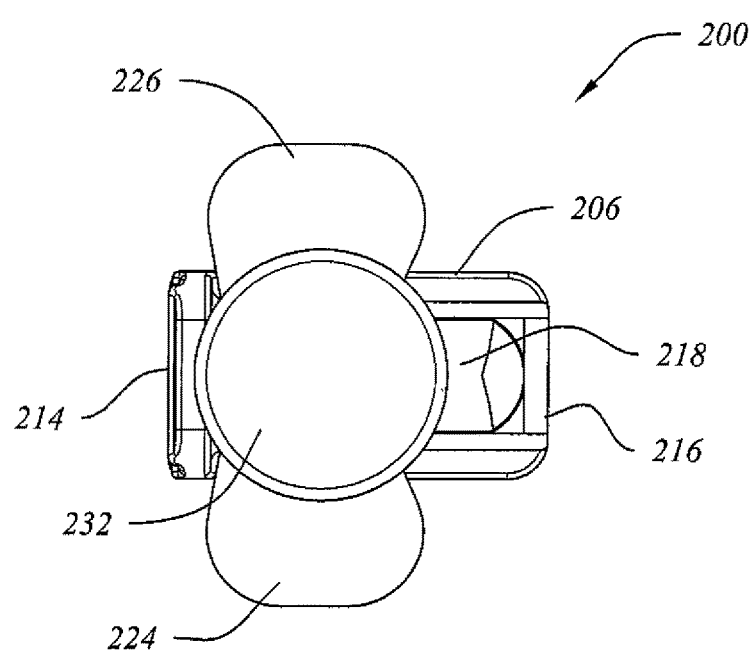
FIG. 33 is a rear elevation view of the medical device of FIG. 31 following removal of the needle cover and also following needle retraction.

Referring to FIGS. 27-29 and 32, a fluid seal such as annular fluid seal 242 is desirably provided to prevent fluid leakage around the fluid pathway 244 (FIG. 27) between opening 248 of connector housing 202 and the rearwardly facing, annular end surface of needle holder 246. In this embodiment, fluid seal 242 is desirably made of a medical grade elastomeric material and is seated inside opening 248 of base 216 of connector housing 202. The length, radius, durometer of fluid seal 242 and the inside diameter of fluid pathway 244 through fluid seal 242 are desirably such that the forwardly facing end of fluid seal 242 can be compressed against the head of needle holder 246 without blocking or overly restricting fluid flow through fluid pathway 244 during use. Referring to FIG. 29, following use of medical device 200, fluid seal 242 is desirably carried by connector housing 202 as connector housing 202 is repositioned relative to frontal attachment 204 to initiate retraction. During this repositioning, the forwardly facing end of fluid seal 242 is desirably moved away from needle holder 246 and into fluid-tight engagement with the opposed, rearwardly facing surface of body 206 (FIG. 32) of frontal attachment 204 to prevent any fluid leakage or flow-back from syringe 222. Although the use of an annular fluid seal 242 as described here is preferred, other similarly effective fluid seals can also be employed within the scope of the invention.

Referring to FIGS. 29-33, following repositioning of connector housing 202 from the first position to the second position as discussed above, needle retraction spring 250 expands rearwardly from needle support 208 and drives needle holder 246 rearwardly into needle retraction cavity 220 inside chamber 218, thereby retracting the front end of needle 210 into needle support 208 or needle retraction cavity 220. The relative lengths of needle support 208, needle retraction cavity 220 and needle retraction spring 250 are desirably cooperatively sized according to the range of needle lengths with which medical device 200 is anticipated to be used.

Although the medical device disclosed herein in relation to the embodiment of FIGS. 24-33 is in many respects similar to that disclosed in relation to the embodiment of FIGS. 1-23, medical device 200 offers several distinct advantages that are only available in an embodiment where an associated medical device such as a syringe is made as an integral portion of the medical device. More particularly, the presence of a syringe barrel in combination with a plunger such as a plunger 228 having a slidable fluid seal such as plunger seal 238 allows the creation of a variable volume fluid chamber such as fluid chamber 240 within one device. Further, the user is afforded the ability to create either a positive or negative pressure inside a fluid delivery or extraction device having a retractable needle and a needle retraction cavity that is not at any time disposed within the fluid pathway. This configuration enables a user to infuse or extract variable volumes of various fluids having various viscosities at variable pressures suitable for the intended application without risk of blowout or premature needle retraction. Further, the subject device provides all the safety benefits associated with one-handed use and retraction with a needle that can be retracted directly from a patient following use and into a safe position where the needle cannot be reused. Further, the simple and compact design, with few moving parts and lower manufacturing and assembly costs, will desirably enhance its potential for widespread use.

Figure 37:
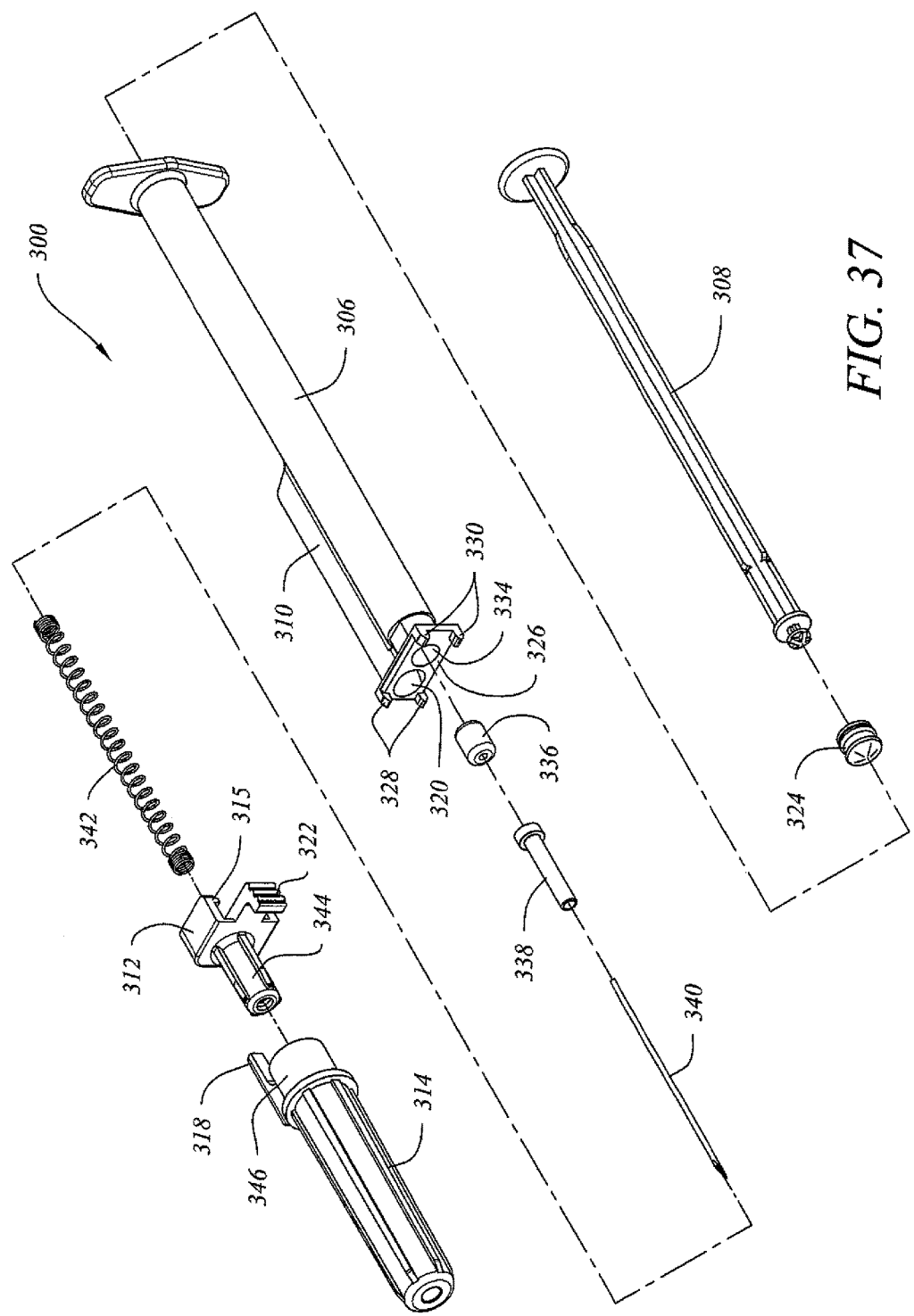
FIG. 37 is an exploded right perspective view of the medical device of FIG. 34.
Figure 38:
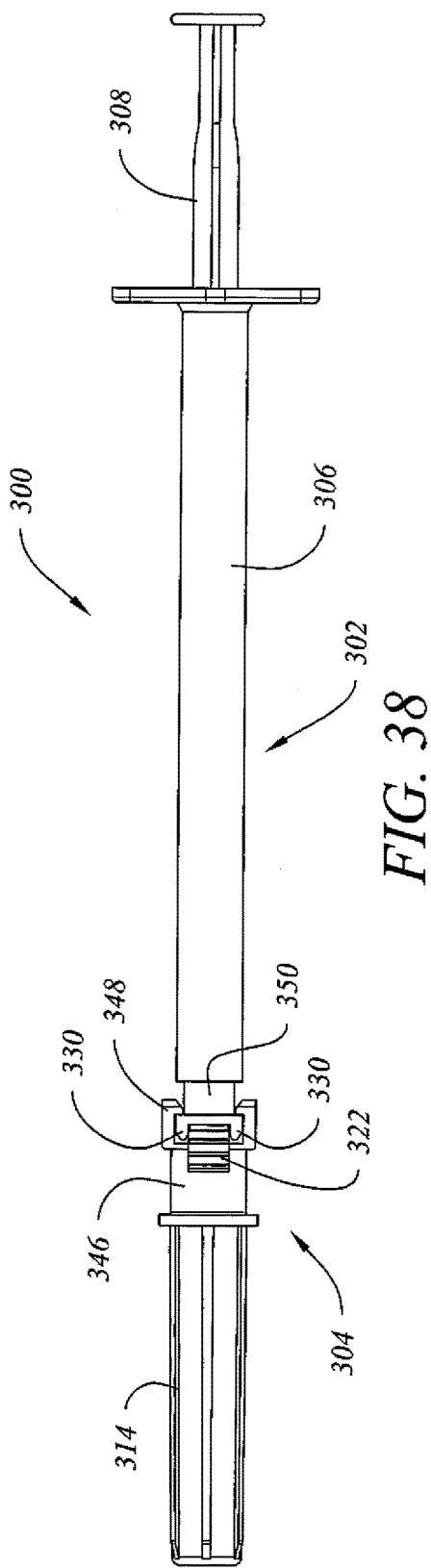
FIG. 38 is a right side elevation view of the medical device of FIG. 34.

Another embodiment of the subject invention is disclosed in relation to FIGS. 34-44 of the accompanying drawings. This embodiment is similar to the embodiment of FIGS. 24-33 in that it comprises a part of an associated medical device that is an integral part of the connector housing. In the embodiment shown in FIGS. 34-44, the associated medical device is a syringe. Referring generally to those drawing figures, medical device 300 desirably comprises a connector housing 302 and frontal attachment 304. Connector housing 302 further comprises generally cylindrical barrel 306 and needle retraction cavity 310 that are molded or otherwise fabricated as a unitary or unitized structure together with base 326 (FIG. 37). Base 326 desirably comprises forwardly facing, laterally spaced-apart openings into needle retraction cavity 320 and into cylindrical bore 334 that communicates with fluid chamber 352 (FIG. 39) disposed inside barrel 306. Opposed stop members 328, 330 (FIG. 37) are provided to limit the range of travel of connector housing 306 (FIGS. 34-36) relative to frontal attachment 304 during needle retraction, as discussed above in relation to medical device 200 of FIGS. 24-33. As shown in FIGS. 34-42, plunger handle 308 with forwardly facing plunger seal 324 is desirably longitudinally slidable inside barrel 306 and can be inserted or withdrawn relative to barrel 306 to vary the volume of fluid chamber 352 as needed for aspiration, injection or extraction through fluid pathway 354 (FIG. 39) communicating with the front end of fluid chamber 352.

Referring to FIGS. 34-37, 43 and 44, frontal attachment 304 desirably further comprises body 312 having a rearwardly facing pair of opposed upper and lower laterally disposed clip members 315 having beveled surfaces adapted to slip over and snap into lateral sliding engagement with upper and lower rails disposed between opposed stop members 328, 330 of base 326 of body 312. As seen in FIG. 44, the square shoulder disposed on the back of each of upper and lower clip members 315 desirably maintain frontal attachment 304 in sliding engagement with body 312 along at least one laterally extending, sliding interface. Annular fluid seal 336 (FIGS. 37, 39 and 42) is desirably provided between connector housing 302 and frontal attachment 304 to limit fluid leakage between them when slidably engaged and when medical device 300 is being used.

Figure 39:
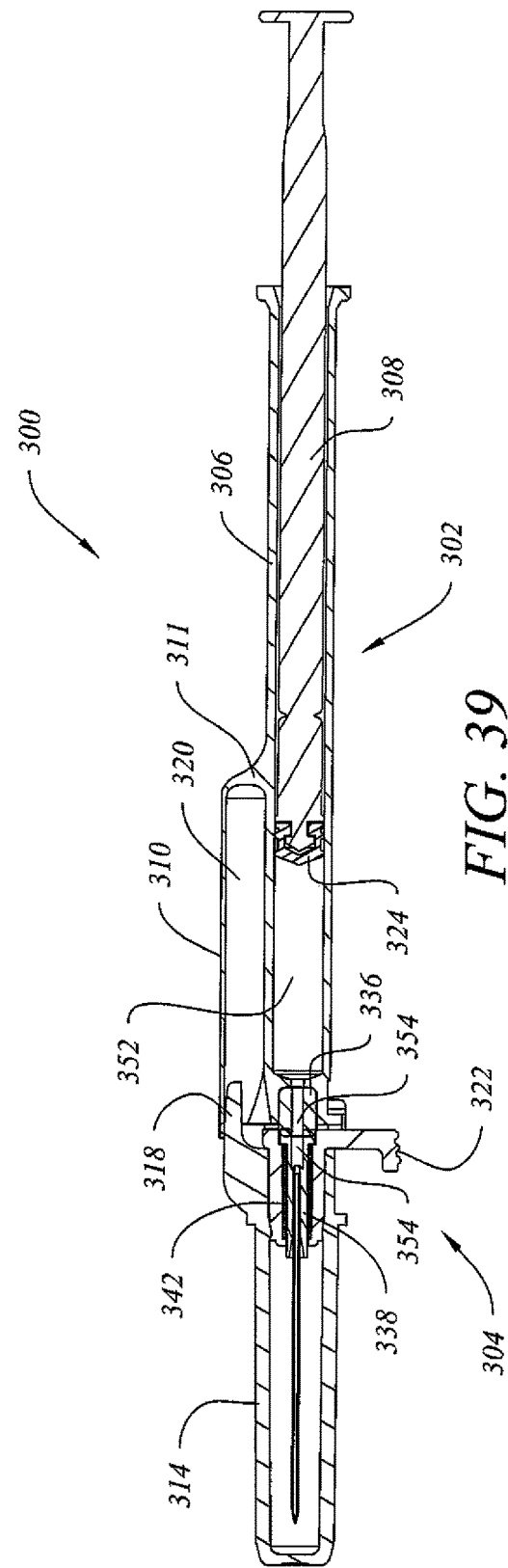
FIG. 39 is a cross-sectional top plan view of the medical device of FIG. 38.
Figure 40:
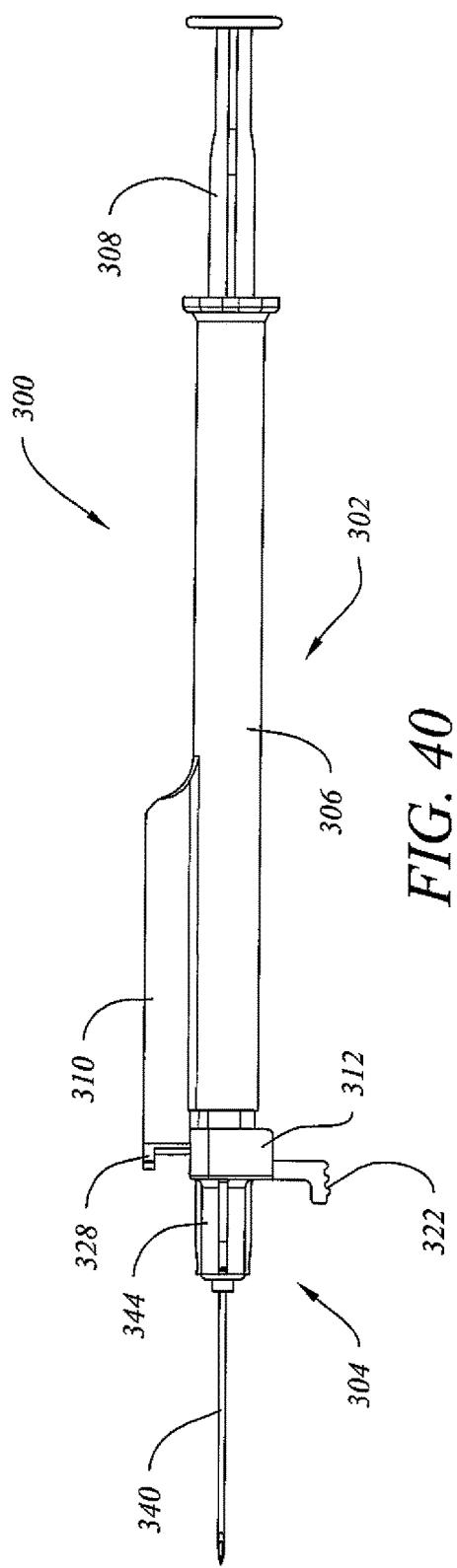
FIG. 40 is a top plan view of the medical device of FIG. 39 with the needle cover removed.
Figure 41:
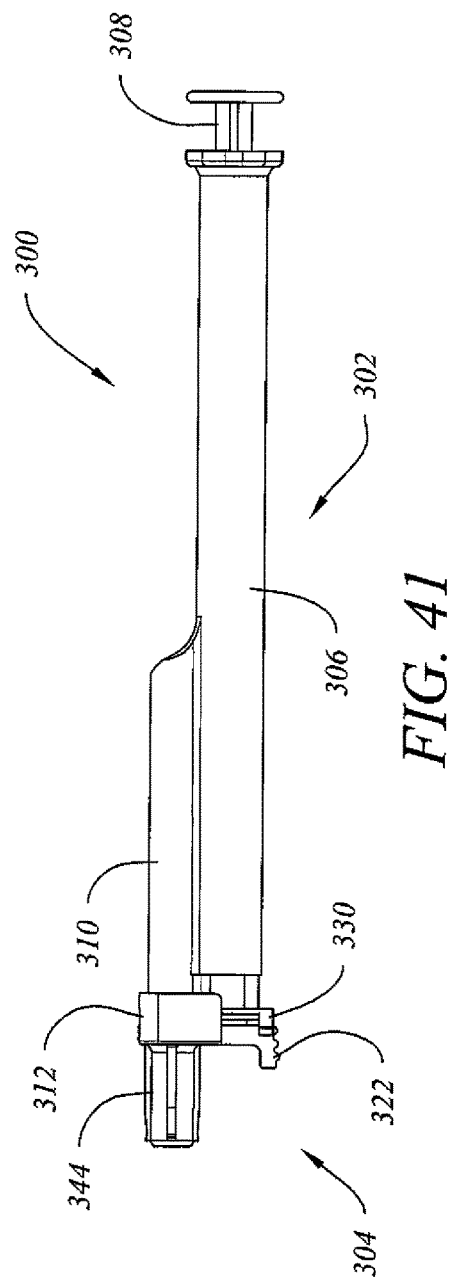
FIG. 41 is a top plan view of the medical device of FIG. 40 with the plunger more fully depressed into the syringe barrel, with the connector housing repositioned laterally relative to the frontal attachment to align the needle retraction chamber and needle retraction cavity with the needle retraction assembly and with the needle retracted.

Referring more particularly to FIGS. 37, 39 and 42, frontal attachment 304 also desirably comprises a needle retraction mechanism comprising needle holder 338 and attached retractable needle 340, and a biasing member such as coil spring 342 exerting a rearwardly directed biasing force against needle holder 338 to facilitate withdrawal of needle 340 from a patient, vial or other fluid source or receptacle during needle retraction as discussed below. The front end of spring 342 is desirably seated inside nose 344 and the elongate portion of needle holder 338 is desirably inserted inside spring 342 and spring 342 is desirably held in compression until frontal attachment 304 is engaged with base 326 of connector housing 302 during assembly. Annular fluid seal 336 is desirably seated inside cylindrical bore 334 (FIG. 37) prior to the attachment of frontal attachment 304 to connector housing 302 and the rearwardly facing surface of needle holder 338 is desirably pressed into abutting engagement with the facing portion of seal 336 by compressed spring 342.

Prior to use, removable needle cover 314 (FIGS. 34 and 37-39) is desirably installed into frictional engagement with nose 344 (FIG. 37) of body 312 to protect needle 340 from being dulled or contaminated and to protect those handling medical device 300 from an inadvertent needle stick prior to use. As shown, needle cover 314 desirably comprises forwardly projecting locking arm 318 that is received into the front opening of needle retraction cavity 320 and prevents premature relative sliding movement between connector housing 302 and frontal attachment 304 prior to use. It will be appreciated, however, upon reading this disclosure that other similarly effective locking devices can also be provided and used to prevent premature lateral shifting or repositioning of connector housing 302 relative to frontal attachment 304 of medical device 300 prior to use.

Frontal attachment 304 desirably further comprises laterally facing textured surface 322 configured for use in applying pressure or resistance force in a direction transverse to the direction of fluid flow through needle 340 and fluid pathway 354 to initiate needle retraction following use. Such pressure or resistance, when combined with oppositely directed pressure applied to some portion of connector housing 302, facilitates lateral repositioning of connector housing 302 relative to frontal attachment 304 to interrupt fluid flow through fluid pathway 354 and initiate needle retraction following use. Lateral movement of connector housing 302 relative to frontal attachment 304 disengages the forwardly facing surface of annular seal 336 from the rearwardly facing surface of needle holder 338 and causes annular seal 336 to slide laterally into engagement with the rearwardly facing surface of body 312, thereby blocking off any fluid flow forwardly from syringe barrel 306 or cylindrical bore 334 subsequent to such repositioning.

Relative lateral movement between connector housing 302 and frontal attachment 304 is limited to travel between a first position (FIG. 35) where needle 340 is forwardly extending from frontal attachment 304 in substantially coaxial alignment with syringe barrel 306 and a second position (FIG. 36) where the needle is retracted to a safe position following use and no longer projects forwardly from nose 344 (FIG. 37) and body 312. As the rearwardly facing head of needle holder 338 moves into substantial coaxial alignment with the front facing opening into needle retraction cavity 320 of needle retraction chamber 310, the rearwardly directed biasing force of spring 342 forces needle holder 338 rearwardly into the closed rear end of needle retraction chamber 310. The rear end of needle retraction chamber 310 can be vented if desired so long as needle holder 338 remains captured inside needle retraction cavity 310. Because spring 342 and needle 340 typically bridge the gap between needle retraction chamber 310 and body 312 of frontal attachment 304, frontal attachment 304 is thereafter held in the second position and cannot be returned to the first position without impermissibly disassembling the used medical device 300.

Importantly, the medical devices disclosed here can be manufactured and assembled with broader tolerances than are otherwise required for conventional medical devices having plunger-activated retractable needles, with an associated reduction in manufacturing cost that can provide a basis for pricing at lower costs for medical providers and consumers. Other benefits are also associated with having a laterally spaced-apart needle retraction cavity and a sequence of operation that does not require cutting, breaking or the use of conventional retainer or holding members disposed between the needle retraction mechanism and a wall of a syringe barrel.

Although luer connectors and compression springs are satisfactory for use in the present invention, it should be understood that other connectors and biasing members can also be used provided that they otherwise meet the general parameters of the invention as disclosed and claimed here. Other alterations and modifications of the invention will likewise become apparent to those of ordinary skill in the art upon reading this specification in view of the accompanying drawings, and it is intended that the scope of the invention disclosed herein be limited only by the broadest interpretation of the appended claims to which the inventors are legally entitled.

We claim:

1. A medical device comprising:
    a connector housing, a frontal attachment, a needle projecting forwardly from the frontal attachment, a needle retraction mechanism, and a locking needle cover;
    the connector housing further comprising a forwardly facing surface with a first opening communicating with a rearwardly facing connector for another associated medical device and a second opening communicating with a rearwardly projecting needle retraction cavity;
    the frontal attachment further comprising a base with a forwardly projecting needle support having a stepped internal bore and a rearwardly facing surface with an opening into the stepped internal bore;
    the forwardly facing surface of the connector housing and the base and rearwardly facing surface of the frontal attachment each further comprising a plurality of cooperatively engaged rails disposed in sliding engagement along at least one sliding interface substantially transverse to the needle and needle retraction cavity with the needle retraction mechanism disposed in the stepped internal bore of the frontal attachment so that the opening into the stepped internal bore is disposed opposite the first opening in the forwardly facing surface of the connector housing and the needle is biased rearwardly by the needle retraction mechanism; and
    the locking needle cover comprising a rearwardly extending locking arm that is inserted into the second opening of the forwardly facing surface of the connector housing to restrict relative sliding movement between the forwardly facing surface of the connector housing and the rearwardly facing surface of the frontal attachment prior to use of the subject medical device;
    whereby the connector housing is engaged with and is slidable in relation to the frontal attachment in a direction substantially transverse to the longitudinal axis through the retractable needle following removal of the locking needle cover and until the connector housing is repositioned by sliding it transversely relative to the frontal attachment to align the needle retraction cavity with the needle and the needle retraction mechanism to initiate retraction of the needle to a safe position with no part of the needle still projecting forwardly from the frontal attachment.

2. The medical device of claim 1 wherein the associated medical apparatus is selected from the group consisting of syringes, vascular catheter insertion devices, fluid infusion sets, and fluid collection devices.

3. The medical device of claim 2 wherein the associated medical apparatus is a syringe.

4. The medical device of claim 1 further comprising a fluid seal disposed between the frontal attachment and the connector housing.

5. The medical device of claim 4 wherein the fluid seal is an annular seal seated in a recess disposed in the first opening in the connector housing.

6. The medical device of claim 4, wherein the fluid seal limits fluid leakage around a fluid pathway between the connector housing and the frontal attachment.

7. The medical device of claim 4 wherein the fluid seal abuts a rearwardly facing end of the needle retraction mechanism.

8. The medical device of claim 1 further comprising a stop that restricts the relative sliding movement.

9. The medical device of claim 1 in which the connector housing has a first position relative to the frontal attachment wherein the needle retraction mechanism is coaxially aligned with the connector.

10. The medical device of claim 9 in which the connector housing has a second position relative to the frontal attachment wherein the second opening is substantially aligned with the needle retraction mechanism.

11. The medical device of claim 9 in which the connector housing has a second position relative to the frontal attachment wherein at least part of the needle retraction mechanism and needle are disposed inside the needle retraction cavity.

12. The medical device of claim 1 wherein the locking needle cover is selectively removable.

13. The medical device of claim 1 wherein the frontal attachment is configured to clip onto the connector housing.

14. The medical device of claim 1 wherein the needle retraction cavity has a rear end that is closed or vented.

* * * * *